(12) United States Patent
Schulz

(10) Patent No.: US 6,232,076 B1
(45) Date of Patent: May 15, 2001

(54) STABILIZER OF DYE SEQUENCING PRODUCTS

(75) Inventor: Vincent P. Schulz, Madison, CT (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 09/498,270

(22) Filed: Feb. 4, 2000

(51) Int. Cl.[7] .............................. C12Q 1/68; C12P 19/34; C07H 21/04
(52) U.S. Cl. ........................... 435/6; 435/91.1; 435/91.2; 536/24.3
(58) Field of Search ............................ 435/6, 91.2, 91.1; 536/24.3

(56) References Cited

U.S. PATENT DOCUMENTS

| | | | |
|---|---|---|---|
| 5,198,537 | 3/1993 | Huber et al. | 530/406 |
| 5,830,657 | * 11/1998 | Leushner et al. | 435/6 |
| 5,840,999 | 11/1998 | Benson et al. | 568/735 |
| 5,847,162 | 12/1998 | Lee et al. | 549/227 |
| 5,861,287 | 1/1999 | Metzker et al. | 435/91.1 |
| 5,945,526 | * 8/1999 | Lee et al. | 536/26.6 |
| 6,008,379 | 12/1999 | Benson et al. | 549/224 |

OTHER PUBLICATIONS

Nagai et al., "Additive Effects of Bovine Serum Albumin DT and . . . ", Biochemistry & Mol. Biol. International, vol. 44 (1), pp. 157–163, Jan. 1998.*

"Automated DNA Sequencing Chemistry Guide," 1998, Perkin–Elmer Corporation.

Metzker et al., 1996, Science 271:1420–1422.

Rosenblum et al., 1997, Nucleic Acids Res. 25:4500–4504.

Hung et al., 1996, Anal. Biochem. 243: 15–27.

"DRAFT"—ABI Prism® 3700 DNA Analyzer Chemistry Guide, 1999, Perkin–Elmer Corporation.

ABI Prism® BigDye™ Terminator Cycle Sequencing Ready Reaction Kit, with AmpliTaq® DNA Polymerase, FS, 1998, Perkin–Elmer Corporation.

* cited by examiner

Primary Examiner—Jeffrey Fredman
Assistant Examiner—Arun Chakrabarti
(74) Attorney, Agent, or Firm—Howell & Haferkamap, LC

(57) ABSTRACT

Methods for reducing degradation of polymerase extension products in the presence of formamide, where the polymerase extension products comprise a nonradioactive detection moiety, are disclosed. The methods comprise adding a base, a buffer or a reducing agent to the polymerase extension products. Sequencing methods which generate polymerase extension products comprising a nonradioactive detection moiety are also disclosed, wherein the degradation of the extension products is reduced or eliminated by the addition of a base, a buffer, or a reducing agent. Compositions for reducing degradation of the above polymerase extension products are also disclosed, where the compositions comprise a base, a buffer, or a reducing agent. Kits for performing sequencing methods are also disclosed, wherein the degradation of polymerase extension products is reduced or eliminated. The kits comprise a base, a buffer, or a reducing agent, and instructions.

21 Claims, 32 Drawing Sheets

STABILIZER OF DYE SEQUENCING PRODUCTS

BACKGROUND OF THE INVENTION (1) Field of the Invention

The present invention generally relates to methods and compositions for stabilizing labeled nucleic acids. More specifically, the invention relates to the stabilization of nucleic acids which are labeled with nonradioactive compounds such as fluorescent dyes for methods such as sequencing.

(2) Description of the Related Art

Nonradioactively labeled nucleic acids generally utilize various compounds covalently attached to a portion of the nucleotide base. These compounds may be detectable by treating the nucleic acid with a specific ligand of the compound, such as an antibody when the compound is a hapten such as digoxigenin. See, e.g., U.S. Pat. No. 6,198, 537. Alternatively, the compounds may be detectable without additional treatment, such as when the compound is a fluorescent dye. Fluorescent dyes have been particularly useful in DNA sequencing applications because the dyes can be detected at very low concentration and they may be easily incorporated into the nucleic acid to be sequenced. See, e.g., U.S. Pat. No. 5,861,287.

Methods for the sequencing of nucleic acids have undergone numerous improvements, such that sequencing is now rapid, routine and available for automated throughput. See, e.g., U.S. Pat. No. 5,861,287 for a review of some available manual and automated sequencing methods.

Of the several approaches to DNA sequence determination, the dideoxy chain termination method of Sanger et al., 1977, *Proc. Natl. Acad. Sci. USA* 74:560–564, is most commonly used and serves as the basis for all currently available automated DNA sequencing protocols. In the dideoxy method, a sequencing reaction mixture is prepared which generally comprises (a) a DNA template comprising a portion which is to be sequenced, (b) a primer which is complementary to a fragment of the DNA template at the 3' end of the portion to be sequenced, (c) unlabeled deoxyribonucleoside triphosphates (dNTPs), (d) at least one dideoxyribonucleoside triphosphate (ddNTP), (e) a dNTP, a primer or ddNTP which is labeled with a detectable moiety such as a radioactive atom (e.g., $^{35}S$ or $^{32}P$) or a fluorescent dye, (f) a DNA polymerase and (g) an aqueous solution comprising a buffer such as Tris-HCl and other components required for polymerase activity such as $Mg^{+2}$. The sequencing reaction mixture is subjected to conditions suitable for annealing of the primer to the 3' end of the portion of the DNA template, followed by polymerase extension of the primer along the DNA template. Each sequencing reaction is stopped when a ddNTP is incorporated at the 3' end of the growing polymerase extension product. The resulting polymerase extension products represent substantially all complementary extension products with a 5' terminus complementary to the 3' end of the portion of the DNA template, and with a 3' terminal dideoxyribonucleotide at any position along the portion of the DNA template. The polymerase extension products are also labeled with the detectable moiety. The polymerase extension products are then subjected to electrophoresis to separate the various extension products by size, and the order of each of the four bases along the portion of the template is determined by determining which dideoxyribonucleotide terminates each sequential polymerase extension product.

Common variations in the basic dideoxy chain termination sequencing method described above result from variations in the source of the DNA used for the template, the source of the primer, the composition of the unlabeled dNTPs, the ratio of dNTPs to ddNTPs, the polymerase used, whether the polymerase extension products are synthesized in a cycled reaction, whether the polymerase extension reactions for all four bases are executed together or separately, the nature of the detectable moiety, whether the polymerase reaction products are purified before electrophoreses, and whether the electrophoresis is performed on a slab gel or in capillaries. See, e.g., Fredrick M. Ausubel et al. (1995), "Short Protocols in Molecular Biology", John Wiley and Sons; Joseph Sambrook et al. (1989), "Molecular Cloning, A Laboratory Manual", second ed., Cold Spring Harbor Laboratory Press; U.S. Pat. No. 5,861,287; and "Automated DNA Sequencing Chemistry Guide," 1998, Perkin-Elmer Corporation.

In some variations of the dideoxy sequencing method, fluorescent dyes are used. These methods are advantageous because the fluorescent dyes are generally highly sensitive yet are not hazardous like radioactive detection moieties. Examples include 5'-tetramethylrhodamine, fluorescein dyes, aromatic-substituted xanthine dyes, 4,7-dichlororhodamine dyes, asymmetric benzoxanthene dyes and BODIPY dyes. See, e.g., U.S. Pat. Nos. 5,840,999; 5,847,162; 6,008,379; Metzket et al., 1996, *Science* 8:1420–1422. Additionally, various fluorescent labels have been developed which vary in emission wavelength maxima and which can be distinguished on that basis. This allows the practitioner to label each ddNTP with a different label in one reaction mixture. Alternatively, the primer for each reaction can be labeled with a different fluorescent dye in a separate reaction mixture for each ddNTP. All four sequencing reactions can then be electrophoresed together and the various terminal fluorescent-labeled ddNTP can be distinguished on the basis of the absorption and emission maxima. An example of dye sets which can be distinguished from each other are the dichlororhodamine dyes ROX, R6G, R110 and TAMRA (TMR), as discussed in Rosenblum et al., 1997, *Nucleic Acids Res.* 25:4500–4504. See Table 1.

Energy transfer fluorescent dyes are dyes which include a donor fluorophore covalently conjugated to an acceptor fluorophore. When the donor fluorophore is excited, the energy emission from the donor is transferred to the acceptor fluorophore causing the acceptor to fluoresce. See, e.g., U.S. Pat. No. 5,945,526; Hung et al., 1996, *Anal. Biochem.* 243:15–27; and Rosenblum et al., supra. See also "Automated DNA Sequencing Chemistry Guide," 1998, Perkin-Elmer Corporation, which discloses energy transfer fluorescent dyes which include BigDye™ dyes. The most commonly used BigDye™ energy transfer dyes comprise one of the dichlororhodamine dyes R110, R6G, TAMRA or ROX as the acceptor dye, and 6-carboxyfluorescein (6-FAM or 6CFB) or 5-carboxyfluorescein (5-FAM or 5CFB) as the donor dye. When used as a label for ddNTPs or primers, the BigDye™ dyes emit the fluorescence at the same wavelength as acceptor dichlororhodamine dyes (530 nm, 565 nm, 595 nm, and 625 nm for R110, R6G, TAMRA, and ROX, respectively) but fluoresce 2–3 times brighter than the dichlororhodamine dyes.

The BigDye™ dyes are used in the Perkin-Elmer® Automated DNA sequencing system. In that system, where the dye is conjugated to the dideoxy terminator nucleotide, the terminator dye combinations are ddT-EO-6CFB-dTMR, ddC-EO-6CFB-dROX-2, ddA-PA-6CFB-dR6G, and ddG-EO-5CFB-dR110, where EO is propargyl ethoxyamino and PA is propargylamino, which are linkers between the ddNTP and the donor 6CFB. See Table 1. Similar reagents are used when the primers rather than the ddNTP terminator has the BigDye™ label.

After the polymerase extension products are synthesized in the sequencing reaction mixture using BigDye labels, Perkin-Elmer® recommends that the primer extension products are purified, e.g., by Sephadex G-50 chromatography and/or ethanol precipitation. The samples are then resuspended in deionized formamide with alkaline EDTA. See "Automated DNA Sequencing Chemistry Guide" supra and "DRAFT—ABI Prism® 3700 DNA Analyzer Chemistry Guide," 1999, Perkin-Elmer Corporation. The formamide keeps the purified polymerase extension products denatured to prevent secondary structures in the primer extension products from affecting the results of the electrophoresis. If water is used instead of formamide, the electrophoretic runs are not as reproducible and random injection failures can occur when capillary electrophoresis is used.

However, Perkin-Elmer has reported that formamide reacts slowly with water to produce formic acid and ammonia, and it is believed that these reaction products react with the polymerase extension products to degrade the sample DNA. "DRAFT—ABI Prism® 3700 DNA Analyzer Chemistry Guide," 1999, Perkin-Elmer Corporation. Such degraded samples are manifested by a reduction in signal strength of the fluorescent detection moiety and/or the presence of nonspecific excess signal, for example at a particular position in a gel of capillary electrophoresis run. To address this problem, Perkin-Elmer® recommends resuspending the purified primer extension products in a loading buffer comprising deionized formamide and alkaline ethylenediaminetetraacetic acid (EDTA) and keeping these resuspended samples covered with foil. Id.

However, Perkin-Elmer® does not further characterize the particular effects caused by the formic acid and ammonia and still recommends that the samples not be left at room temperature for more than 24 hours even when deionized formamide with EDTA are used. This 24 hour limitation can limit the utilization of the capacity of high-throughput sequencers such as the ABI3700 capillary DNA sequencer. For example, when 384-well plates are used with the PE Biosystems ABI Prism® 3700 DNA Analyzer, a 96-well batch can be processed in about four hours. The 384-well plate is thus analyzed in four 96-well batches taking about 16 hours. An analysis of two 384-well plates would thus take about 32 hours, well beyond the 24 hour recommended limitation. Additionally, the inventor has noted that purified polymerase extension products comprising a BigDye™ fluorescent detection moiety are inadequately protected from formamide degradation products by the recommended deionized formamide with EDTA loading buffer even when the primer extension products are in room temperature for less than 24 hours.

Consequently, there is a need for additional measures which would prevent the breakdown of polymerase extension products by formamide or other denaturants. Although this need is particularly acute for polymerase extension products comprising BigDye™ detection moieties, such measures would likely stabilize polymerase extension products comprising other detection moieties, particularly other fluorescent dyes.

SUMMARY OF THE INVENTION

Accordingly, the inventor herein has succeeded in discovering that degradation of polymerase extension products in the presence of formamide, wherein the products comprise a nonradioactive detection moiety, can be reduced or alleviated by the addition of a compound comprising a base, a buffer or a reducing agent. Examples of a useful base, buffer, and reducing agent for this purpose are 0.3 mM $NaHCO_3$, 0.3 mM Tris pH 9.0 and 10 mM dithiothreitol, respectively. Surprisingly, the addition of the compound reduces or eliminates degradation of polymerase extension products. The application of this discovery is particularly useful in sequencing reactions, in particular automated sequencing reactions, especially when the nonradioactive detection moiety is a fluorescent energy transfer dye, in particular Perkin-Elmer BigDye™ fluorescent energy transfer dyes.

Thus, one embodiment of the present invention is directed to a method of reducing degradation of fluorescent dye-labeled polymerase extension products in the presence of formamide. The method comprises adding to the extension products at least one compound selected from the group consisting of a base, a buffer and a reducing agent, wherein the compound is not EDTA.

In an additional embodiment, the present invention is directed to a method for determining the sequence of a DNA template. The method comprises
 (a) preparing a sequencing reaction mixture comprising
  (i) the DNA template;
  (ii) a primer which is complementary to a 3' region of the DNA template;
  (iii) unlabeled deoxyribonucleoside triphosphates;
  (iv) at least one dideoxyribonucleoside triphosphate;
  (v) a DNA polymerase;
  (vi) a substance labeled with a fluorescent dye, wherein the substance is a deoxyribonucleoside triphosphate, a primer or the at least one dideoxyribonucleoside triphosphate; and
  (vii) an aqueous buffer;
 (b) treating the sequencing reaction mixture under conditions and for a time sufficient to synthesize a series of polymerase extension products of different lengths, wherein each of the polymerase extension products comprises a sequence of nucleotides complementary to at least part of the DNA template and wherein at least one of the nucleotides in each extension product comprises the fluorescent dye;
 (c) mixing the purified polymerase extension products with a denaturing solution comprising formamide, wherein the denaturing solution further comprises at least one compound that reduces degradation of the nucleotide comprising the fluorescent dye, wherein the compound is not alkaline ethylenediaminetetraacetic acid (EDTA); and
 (d) analyzing the denatured polymerase extension products to determine the sequence of nucleotides in the portion of the DNA template. Preferred compounds in the denaturing solution are bases, buffers, and reducing agents.

The present invention is also directed to a mixture of purified polymerase extension products and a denaturing solution, where the polymerase extension products comprise a nucleotide labeled with a fluorescent dye and wherein the denaturing solution comprises formamide and at least one compound that reduces degradation of a labeled nucleotide, wherein the at least one compound is not alkaline ethylenediaminetetraacetic acid.

The present invention is additionally directed to an improvement in a method for determining the sequence of a portion of a DNA template, wherein the DNA template comprises nucleotides, and the method comprises (a) preparing a sequencing reaction mixture comprising
    (i) the DNA template;
    (ii) a primer which is complementary to a 3' region of DNA template;
    (iii) unlabeled deoxyribonucleoside triphosphates;
    (iv) at least one dideoxyribonucleoside triphosphate;
    (v) a DNA polymerase;
    (vi) a substance labeled with a fluorescent dye, wherein the substance is a deoxyribonucleoside triphosphate, the primer or the at least one dideoxyribonucleoside triphosphate; and
    (vii) an aqueous buffer;
(b) treating the sequencing reaction mixture under conditions and for a time sufficient to synthesize a series of polymerase extension products of different lengths, wherein each of the polymerase extension products comprises a sequence of nucleotides complementary to at least part of the DNA template and wherein at least one of the nucleotides in each extension product comprises the fluorescent dye;
(c) mixing the polymerase extension products with a denaturing solution comprising formamide;
(d) analyzing the treated sequencing reaction mixture of step (c) to determine the sequence of nucleotides in the DNA template, wherein the improvement comprises including in the denaturing solution of step (c) at least one compound that reduces degradation of the nucleotide comprising the fluorescent dye, wherein the at least one compound is not alkaline EDTA.

In an additional embodiment, the present invention is directed to a kit for practicing the above methods. The kit comprises at least one compound selected from the group consisting of a base, a buffer, and a reducing agent, as well as instructions directing the use of the at least one compound to reduce degradation of polymerase extension products in a formamide denaturing solution, wherein the extension products comprise a fluorescent dye and wherein the at least one compound is not alkaline EDTA. The kit can comprise any additional component used in the above methods.

Among the several advantages achieved by the present invention, therefore, may be noted the provision of methods for reducing or eliminating degradation of polymerase extension products which contain a nonradioactive detection moiety, wherein the extension products are in a formamide solution; the provision of compositions comprising polymerase extension products which further comprise a compound which reduces or eliminates degradation of the polymerase extension products; the provision of improvements in sequencing methods, including automated sequencing methods, wherein the degradation of polymerase extension products is reduced or eliminated; and the provision of kits containing components which reduce the degradation of polymerase extension products.

BRIEF DESCRIPTION OF THE DRAWINGS

In all of the figures, the arrow indicates the capillary electrophoresis results of polymerase extension products which are about 90 bases long, or degradation products which comigrate with such polymerase extension products.

DESCRIPTION OF THE PREFERRED EMBODIMENTS

Figure 1:
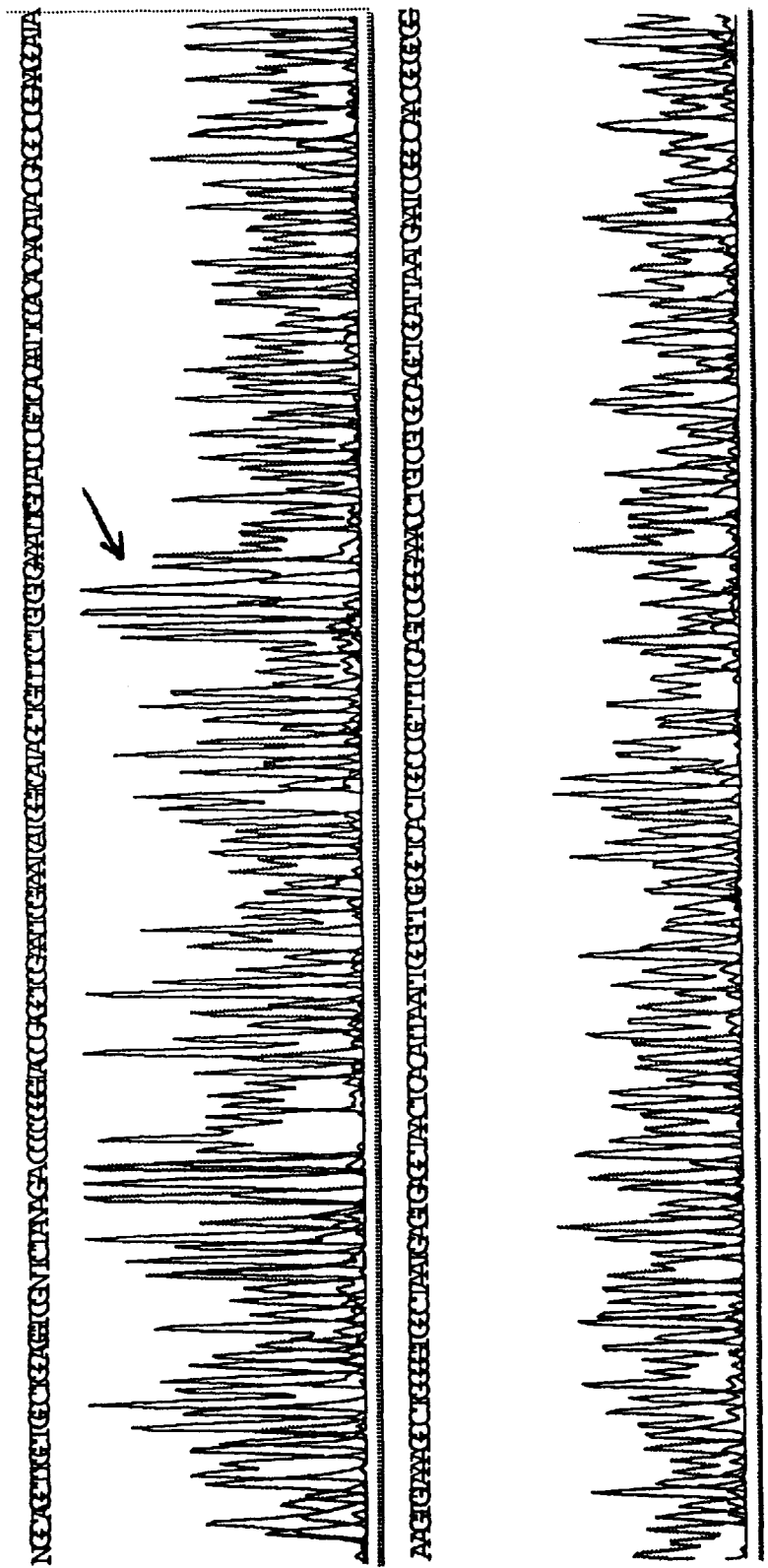
FIG. 1 depicts the results of an automated capillary electrophoresis sequencing run, wherein the polymerase extension product denaturing solution contained formamide and alkaline EDTA, and wherein the capillary electrophoresis was performed immediately after suspending the polymerase extension product in the denaturing solution. No degradation of the polymerase extension products is evident.
Figure 1A:
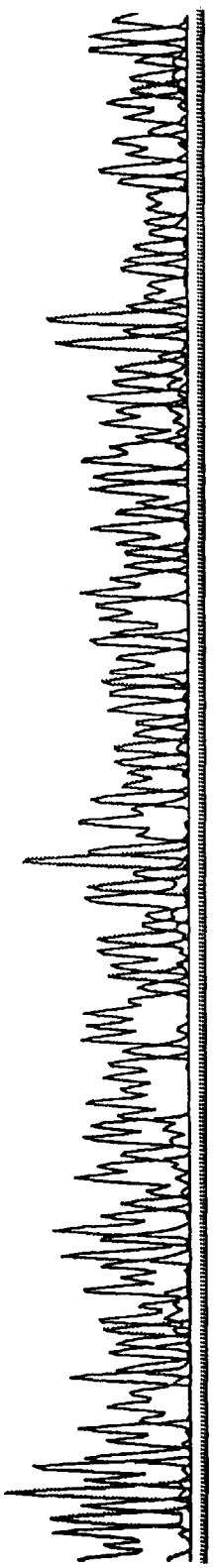
Figure 1A:
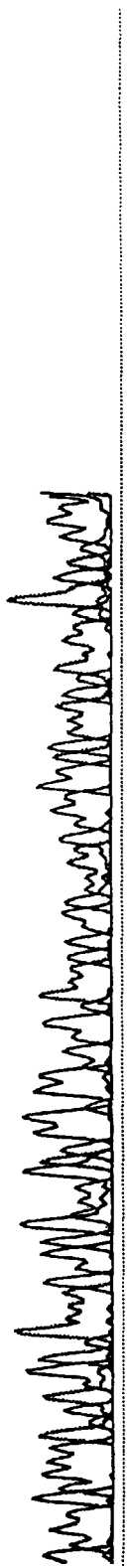
Figure 3:
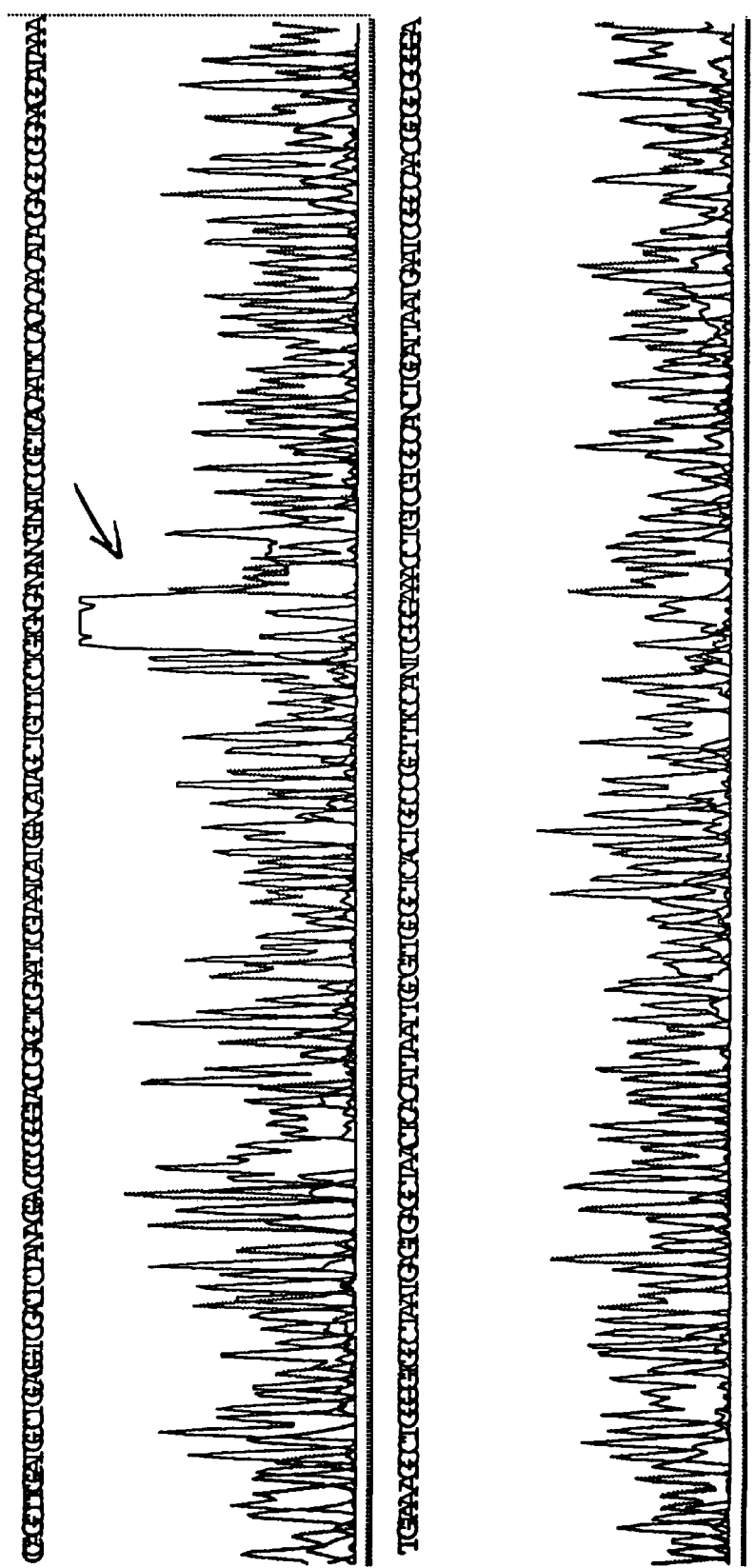
FIG. 3 depicts the results of an automated capillary electrophoresis sequencing run, wherein the polymerase extension product denaturing solution contained formamide and alkaline EDTA, and wherein the capillary electrophoresis was performed 21 hours after suspending the polymerase extension product in the denaturing solution. As compared to the undegraded sample in FIG. 1, severe degradation of the polymerase extension products is evident.
Figure 3A:
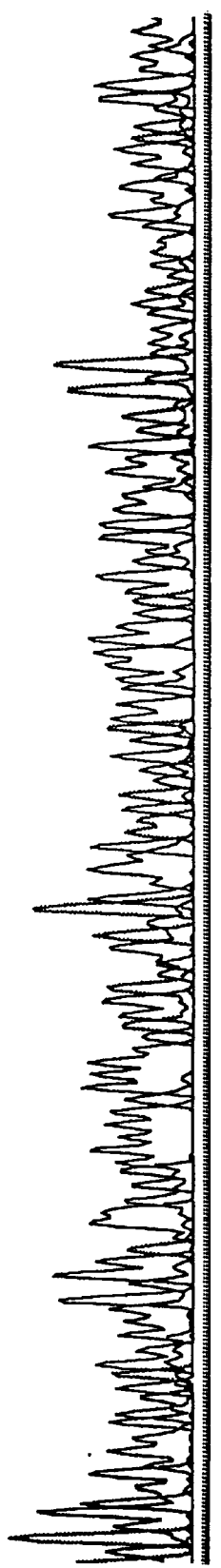
Figure 3A:
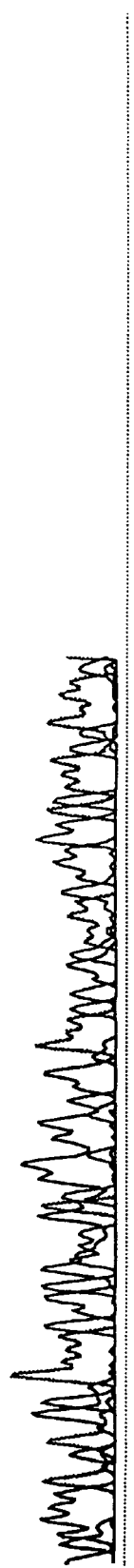

The present invention is based on the discovery that degradation of polymerase extension products in the presence of formamide, wherein the polymerase extension products comprise a nonradioactive detection moiety such as a fluorescent dye, can be reduced or alleviated by the addition of a compound comprising a base, a buffer or a reducing agent. Without being held to any particular theory, it is believed that the formamide breakdown products formic acid and ammonia induce the primer extension product degradation through acidification and that the degradation results from the removal of the detection moiety from a nucleotide base. The degradation of polymerase extension products is manifested as a reduction in signal strength of the nonradioactive detection moiety and/or the presence of nonspecific excess signal, for example at a particular position in a gel or capillary electrophoresis run. See, e.g. FIG. 3, representing the results of a capillary electrophoresis run of sequencing polymerase extension products comprising BigDye™ fluorescent labels, where degradation of the G-terminating polymerase extension products is evident as a reduction in signal strength (compared to the electrophoretic results of the undegraded products of FIG. 1) and the presence of excessive G label which comigrates with polymerase extension products which are about 90 bases long (arrow).

As used herein, the term "polymerase extension product" is a product of polymerase extension of a template nucleic acid. A preferred polymerase extension product is a deoxyribonucleic acid (DNA), but ribonucleic acid (RNA) extension products are also applicable. The nucleotides in the polymerase extension product can be the common nucleotides which naturally occur in genomic DNA and RNA, i.e., the monophosphates of deoxyadenosine, deoxyguanosine, deoxycytidine, deoxythymidine, adenosine, guanosine, cytidine, and uridine. The polymerase extension product can also include other nucleotides which may be useful replacements for any of the above. Non-limiting examples are deoxyinosine monophosphate and 7-deaza-deoxyguanosine monophosphate. As is well known, nucleotides which are particularly useful for polymerase extension products used in sequencing procedures are 3' terminal dideoxyribonucleotides such as dideoxyguanosine, dideoxyadenine, dideoxycytidine and dideoxythymidine. The skilled artisan can readily further identify which nucleotides are useful for any particular polymerase extension product application.

The polymerase extension products further comprise a nonradioactive detection moiety which is greater than about 300 Daltons. The nonradioactive detection moiety can be a molecule which requires further processing to detect, such as digoxigenin, which requires treatment with an anti-digoxigenin antibody to detect its presence. See, e.g., U.S. Pat. No. 5,198,537. Preferably, however, the nonradioactive detection moiety is one that can be detected directly, such as a dye. More preferred detection moieties are fluorescent dyes such as 5'-tetramethylrhodamine, fluorescein dyes, aromatic-substituted xanthine dyes, 4,7-dichlororhodamine dyes, asymmetric benzoxanthene dyes and BODIPY dyes. See, e.g., U.S. Pat. Nos. 5,840,999, 5,847,162 6,008,379 and Metzket et al., supra. Most preferred nonradioactive detection moieties of the present invention are energy transfer fluorescent dyes, including BigDye™ dyes. The most commonly used BigDye™ energy transfer dyes comprise one of the dichlororhodamine dyes ROX, R6G, R110 or TMR as the acceptor dye, and 6-carboxyfluorescein (6-FAM or 6CFB) or 5-carboxyfluorescein (5-FAM or 5CFB) as the donor dye. The nonradioactive detection moieties are preferably conjugated to the polymerase extension products on the base of a deoxyribonucleotide or dideoxyribonucleotide. See Table 1 for the structures of representative dideoxyribonucleotides comprising BigDye™ fluorescent energy transfer dyes. Methods for conjugating various nonradioactive detection moieties to nucleoside bases are well known. See, e.g., U.S. Pat. Nos. 5,298,537 and 5,945,526. Fluorescent energy transfer dyes are preferred for the present invention because, when the proper excitation and emission wavelengths are utilized, they are 2–3-fold brighter than the analogous acceptor dye alone, or other fluorescent dyes. Also, fluorescent energy transfer dyes are particularly susceptible to the problem solved by the present invention. It is also preferred that at least one of the labeled deoxyribonucleotides or dideoxyribonucleotides comprises the fluorescent energy transfer dye EO-5CFB-dR110-2, as in the ddG-EO-5CFB-dR110-2 of Table 1, which is highly susceptible to the problem solved by the present invention, where EO is a propargyl ethoxyamino linker. For example, sequencing electrophoresis of a polymerase extension product comprising ddG-EO-5CFB-dR110-2 in formamide which is first exposed to air for 21 hours yields a result in which the G signal is noticeably reduced and which contains an excess signal at the emission wavelength of 5CFB-dR110-2 which interferes with base determination at about base 90. Compare FIG. 3 (21 hour exposure before electrophoresis) with FIG. 1 (no exposure before electrophoresis). This excess signal at about base 90 occurs whether the sequencing electrophoresis is performed in capillaries (as in FIG. 3) or in gels. Also accompanying this excess signal is a reduction in the signal strength of all G-terminating polymerase extension products. Without being held to any particular theory, it is believed that the utilization of the 5-carboxy isomer of 4'-aminomethylfluorescein in EO-5CFB-dR110-2 rather than the 6-carboxy isomer (present in the other BigDye terminators in Table 1) is a contributing factor to the susceptibility of BigDye-containing polymerase extension products to degradation in the presence of formamide.

TABLE 1

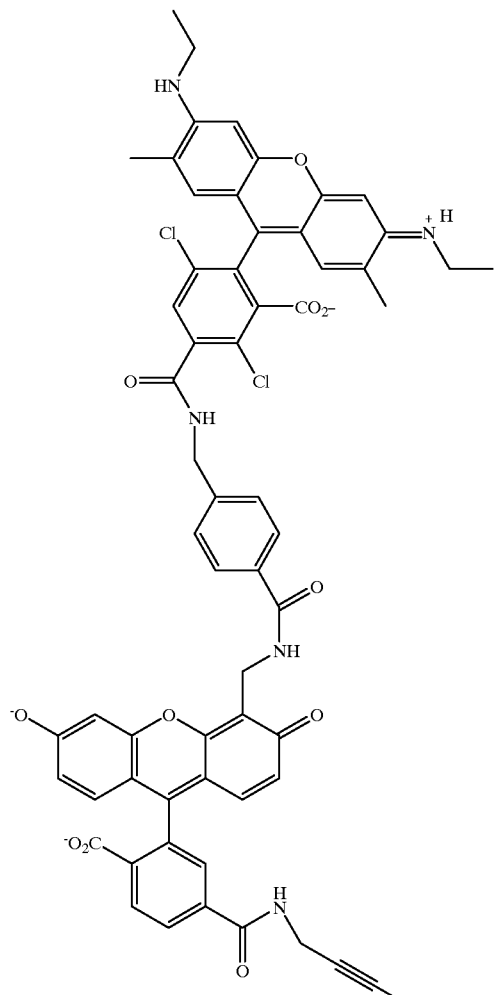

ddATP-PA-6CFB-dR6G-2

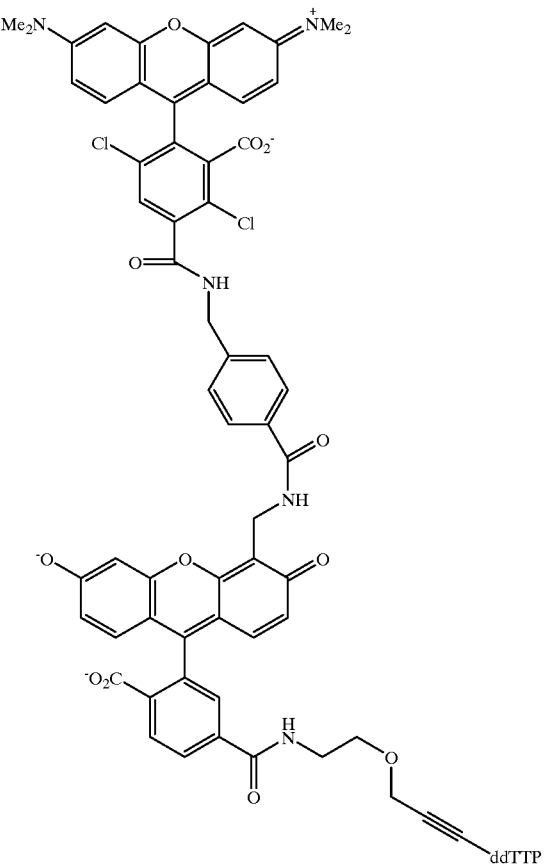

ddT-EO-6CFB-dTMR

TABLE 1-continued

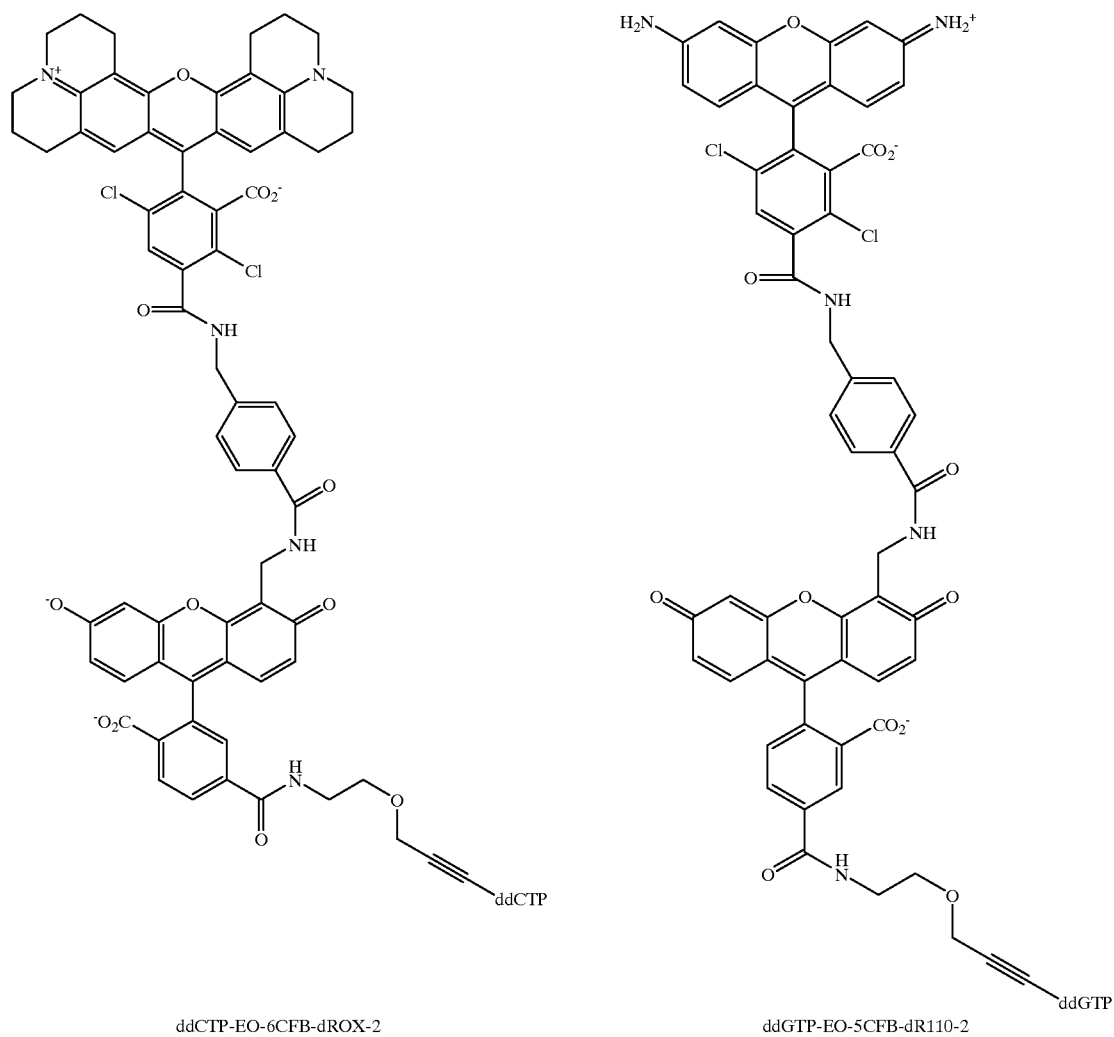

| ddCTP-EO-6CFB-dROX-2 | ddGTP-EO-5CFB-dR110-2 |

The nonradioactive detection moiety can be introduced into the polymerase extension product by any method known in the art. Preferably, the detection moiety is first conjugated to a dNTP or a ddNTP and introduced into the polymerase extension product by including the conjugated dNTP or ddNTP in the polymerase extension reaction which creates the polymerase extension product. The detection moiety can also be present on a primer used to prime the polymerase extension reaction. See, e.g., PE Applied Biosystems Automated DNA Sequencing Chemistry Guide.

The present invention is not narrowly limited to utilization in conjunction with any particular method of making the polymerase extension product or to the use of any particular polymerase in those methods. Nonlimiting examples of useful methods include reverse transcription of an RNA template to make DNA extension products using reverse transcriptase, transcription of DNA template into an RNA using SP6, T3 or T7 DNA-dependent RNA polymerase, or, preferably, replication of a DNA template into a DNA polymerase extension product using a DNA polymerase. As is known in the art, this latter method can comprise a reaction where the template is replicated once, for example using the Klenow fragment of *E. coli* DNA polymerase I or Sequenase™, or a reaction where the template is replicated multiple times in a cycling reaction using a thermostable DNA polymerase such as Taq polymerase or any of the modified versions of thermostable polymerases such as AmpliTaq®.

In some embodiments, the present invention is directed to a method of reducing degradation of fluorescent dye-labeled polymerase extension products in the presence of formamide. The method comprises adding to the extension products at least one compound selected from the group consisting of a base, a buffer and a reducing agent. As used herein, the term "compound" refers to one of a base, a buffer or a reducing agent. Where two or more of such compounds are used in the method, they may be added to the extension products separately or as a mixture. In this and other embodiments of the invention, the base, buffer, or reducing agent can be any such compounds in quantities which do not substantially interfere with the subsequent use of the extension products. For example, 10 mM concentrations of compounds which are ionic may compete with the polymerase extension products for electrophoretic injection in sequencing procedures involving capillary electrophoresis. See, "DRAFT—ABI Prism® 3700 DNA Analyzer Chemistry Guide," 1999, Perkin-Elmer Corporation.

Bases, buffers, or reducing agents which are useful for the present invention may be easily determined by the skilled artisan without undue experimentation. To determine the usefulness of any particular base, buffer or reducing agent, results achieved with and without the base, buffer or reducing agent are compared. Degraded polymerase extension products exhibit a reduction in signal strength of a nonradioactive detection moiety and/or the presence of nonspecific excess signal, for example at a particular position in a gel or capillary electrophoresis run.

Nonlimiting examples of bases which could be utilized in the present invention include sodium hydroxide, potassium hydroxide, sodium metasilicate, calcium carbonate, trisodium phosphate, sodium carbonate, sodium bicarbonate, sodium sesquicarbonate and ferrous hydroxide. A preferred base is sodium bicarbonate ($NaHCO_3$), at a concentration of 0.05–3 mM. More preferably, the sodium bicarbonate concentration is 0.1–1 mM, even more preferably, 0.2–0.5 mM. The most preferred concentration of sodium bicarbonate for the present invention is 0.3 mM.

Nonlimiting examples of buffers which could be utilized in the present invention include the Good buffers (Good et al., 1966, *Biochemistry* 5: 467; Good et al., 1972, *Meth. Enzymol.* 24B: 53; Ferguson et al., 1980, *Anal. Biochem.* 104: 300)—BES, BICINE, CAPS, EPPS, HEPES, MES, MOPS, PIPES, TAPS, TES, TRICINE or TRIS. Other useful buffers include ACES, ADA, 2-amino-2-methyl-1,3-propanediol, 2-amino-2-methyl-1-propanol, 3-amino-1-propanesulfonic acid, AMPSO, BIS-TRIS, BIS-TRIS Propane, CABS, CAPSO, CHES, DIPSO, ethanolamine, glycine, gly-gly, HEPBS, HEPPSO, imidazole, MOBS, MOPSO, POPSO, TABS, TAPSO, triethanolamine, tetroxalate, tartarate, phthalate, phosphate, borax and calcium hydroxide. Various characteristics of these buffers are well known and may be found in the 1999 Sigma® Chemical Company Catalog, Sigma Chemical Company, St. Louis, Mo. A preferred buffer is Tris, pH 9.0, at a concentration of 0.05–3 mM. More preferably, the Tris concentration is 0.1–1 mM, even more preferably, 0.2–0.5 mM. The most preferred concentration of Tris for the present invention is 0.3 mM.

Figure 7:
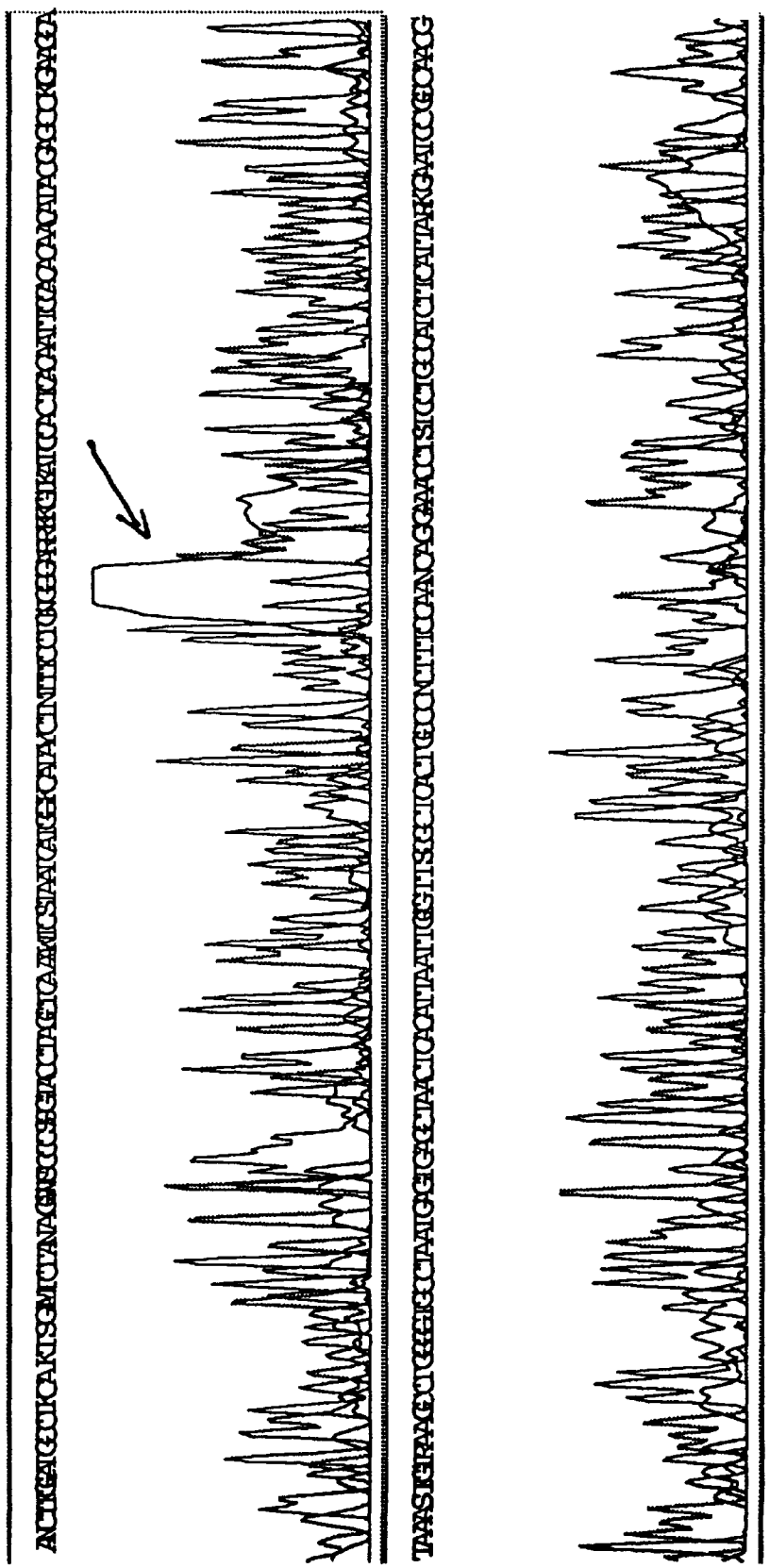
FIG. 7 depicts the results of an automated capillary electrophoresis sequencing run, wherein the polymerase extension product denaturing solution contained formamide and alkaline EDTA, and wherein the capillary electrophoresis was performed 15 hours after suspending the polymerase extension product in the denaturing solution. As compared to the undegraded sample in FIG. 1, severe degradation of the polymerase extension products is evident.
Figure 7A:
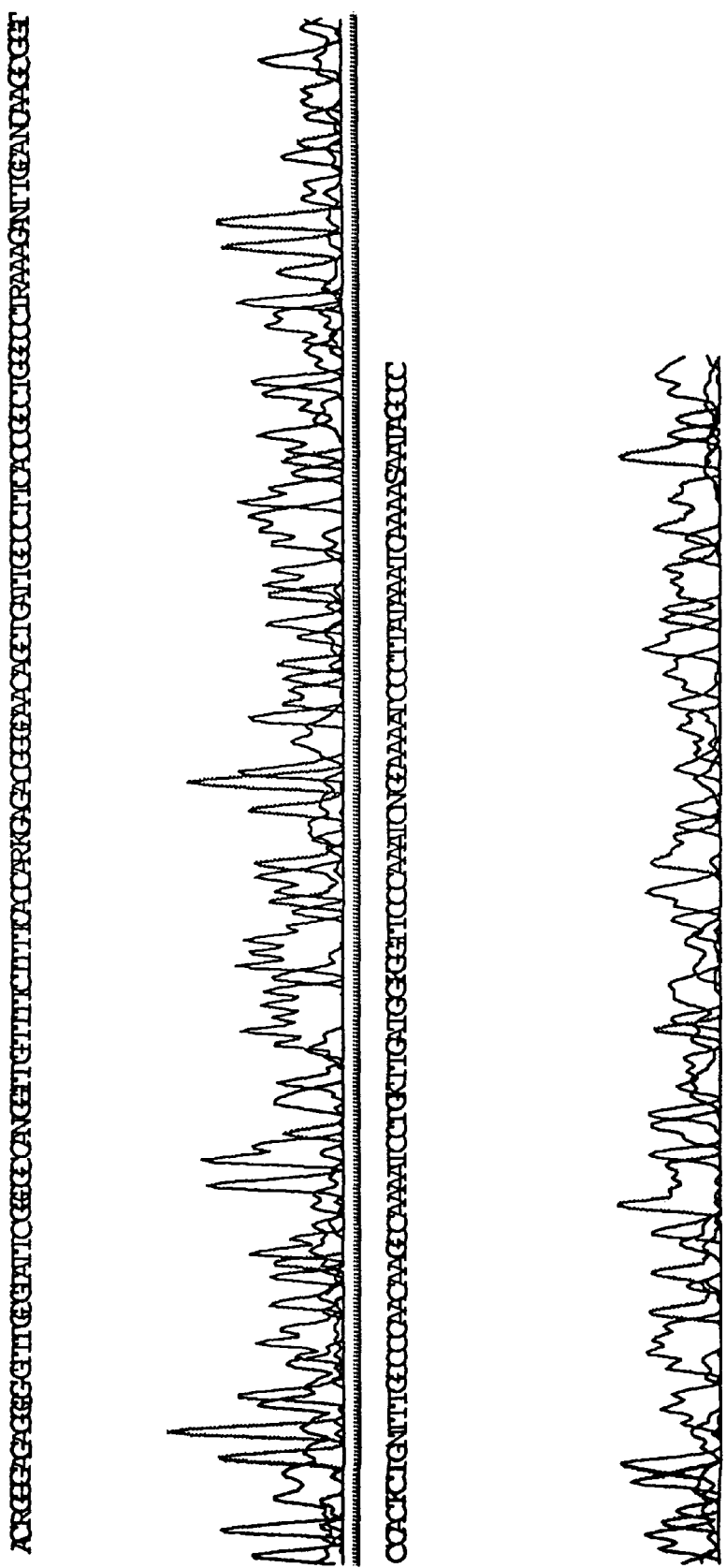
Figure 8:
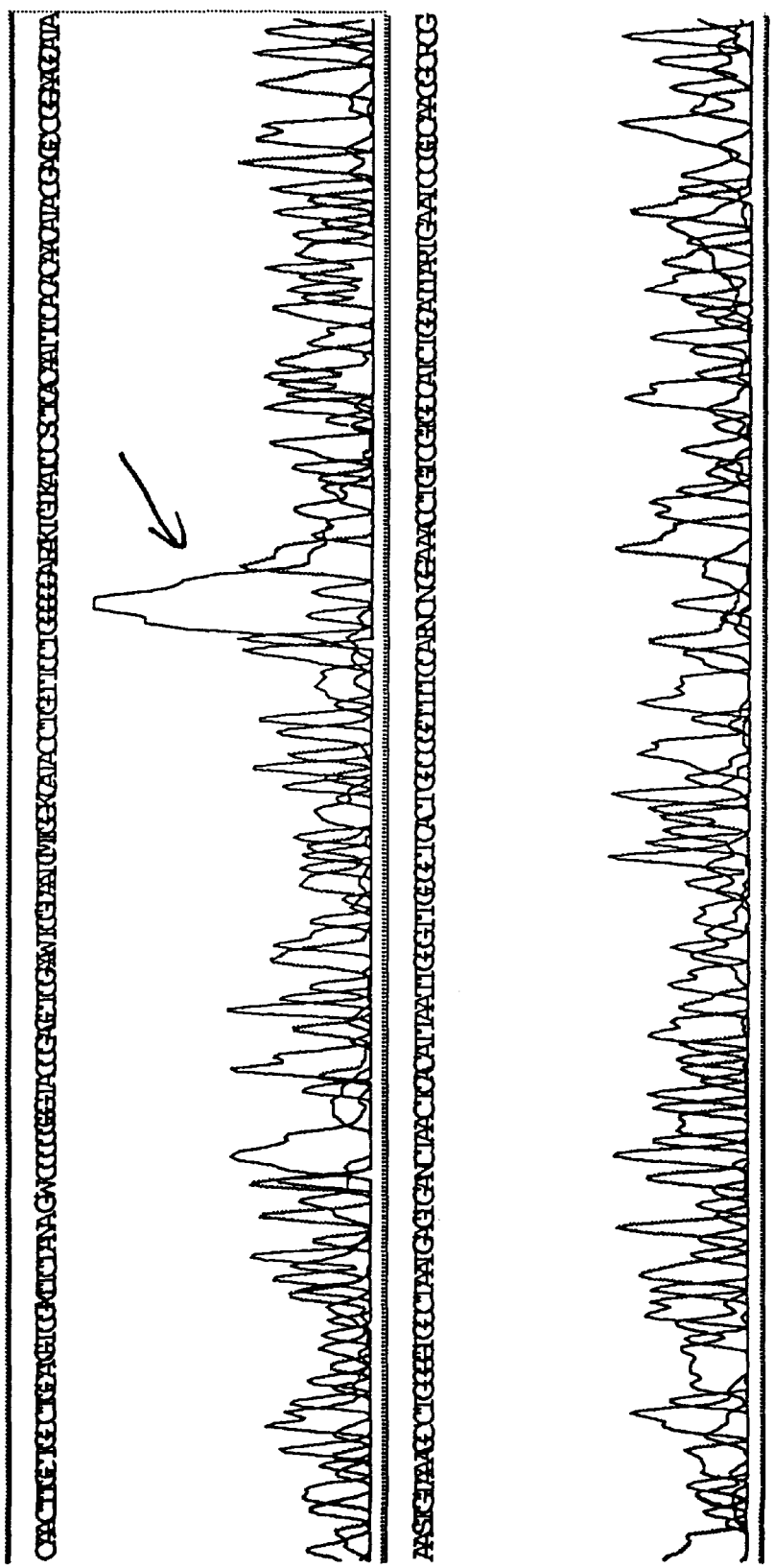
FIG. 8 depicts the results of an automated capillary electrophoresis sequencing run, wherein the polymerase extension product denaturing solution contained formamide, alkaline EDTA, and 1 mM DTT, and wherein the capillary electrophoresis was performed 15 hours after suspending the polymerase extension product in the denaturing solution. As compared to the undegraded sample in FIG. 1, severe degradation of the polymerase extension products is evident.
Figure 8A:
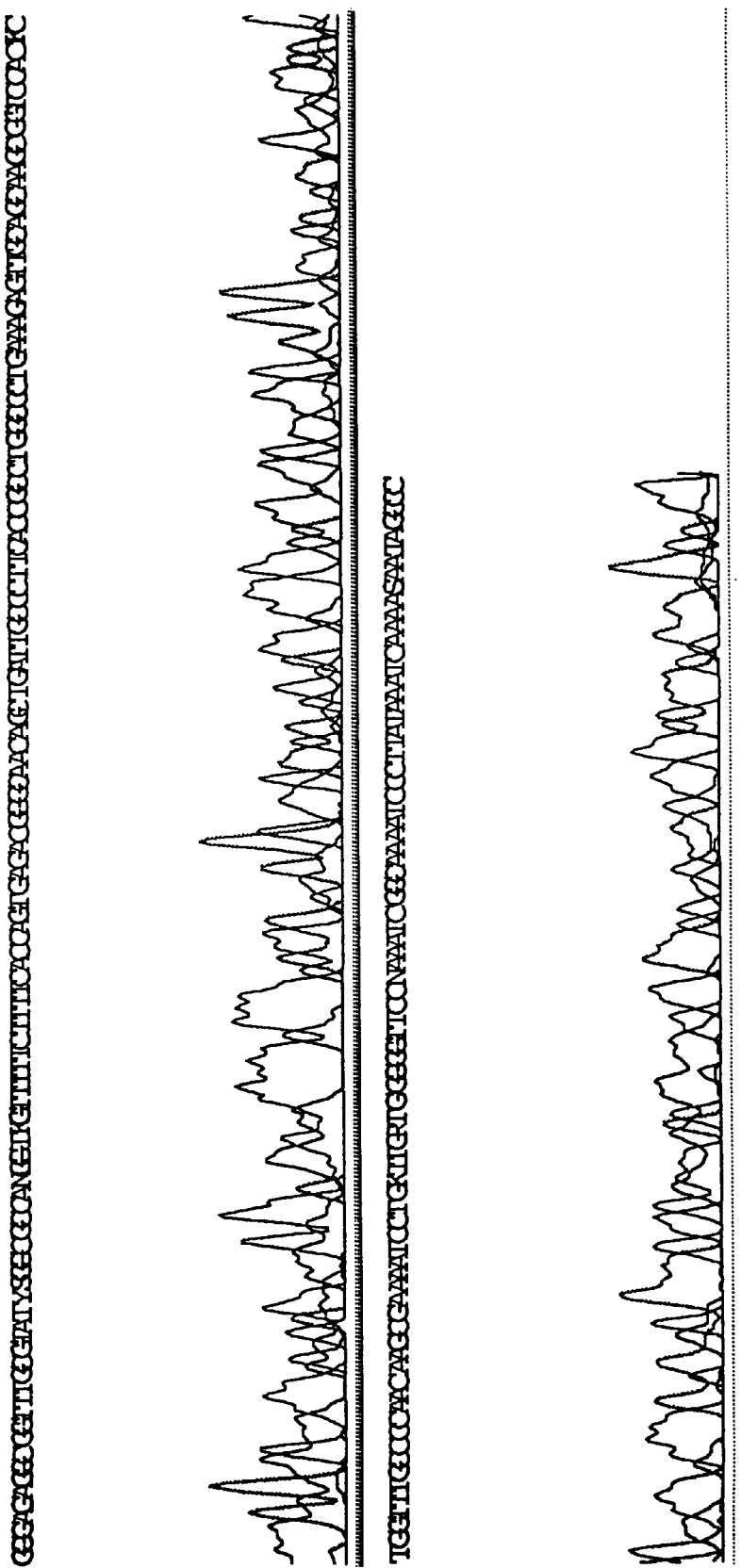
Figure 9:
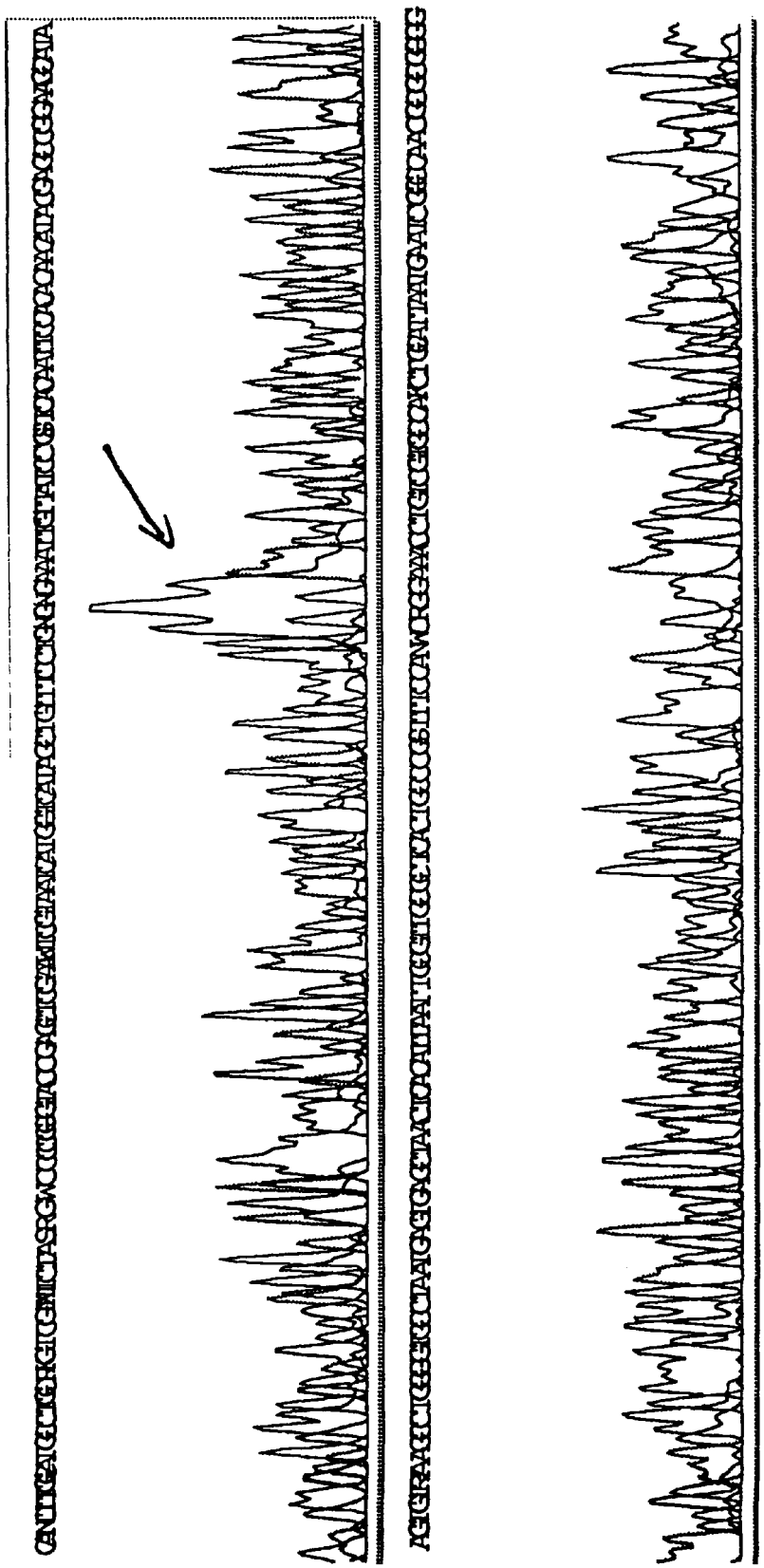
FIG. 9 depicts the results of an automated capillary electrophoresis sequencing run, wherein the polymerase extension product denaturing solution contained formamide, alkaline EDTA, and 2.5 mM DTT, and wherein the capillary electrophoresis was performed 15 hours after suspending the polymerase extension product in the denaturing solution. As compared to FIG. 7, reduced degradation of the polymerase extension products is evident.
Figure 9A:
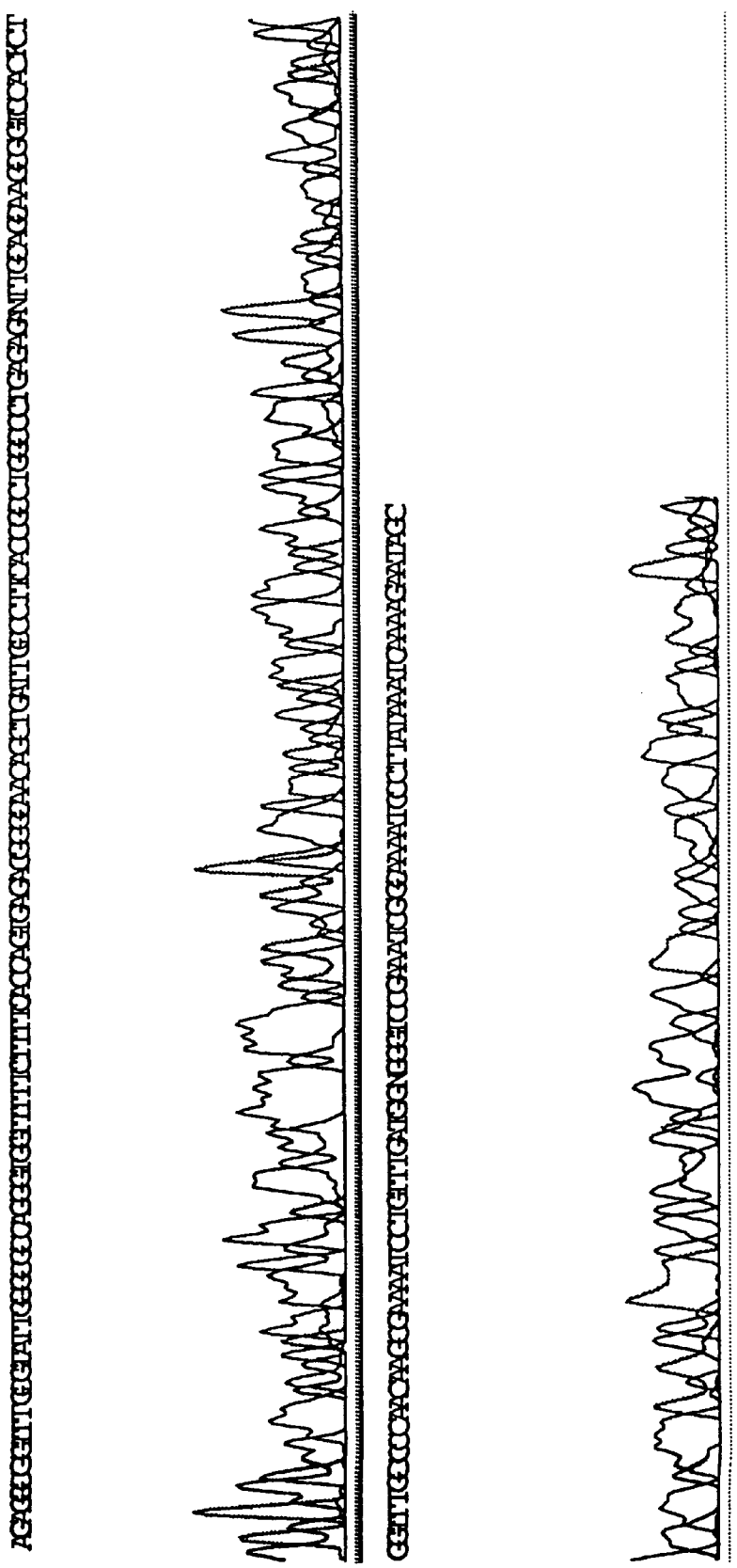
Figure 10:
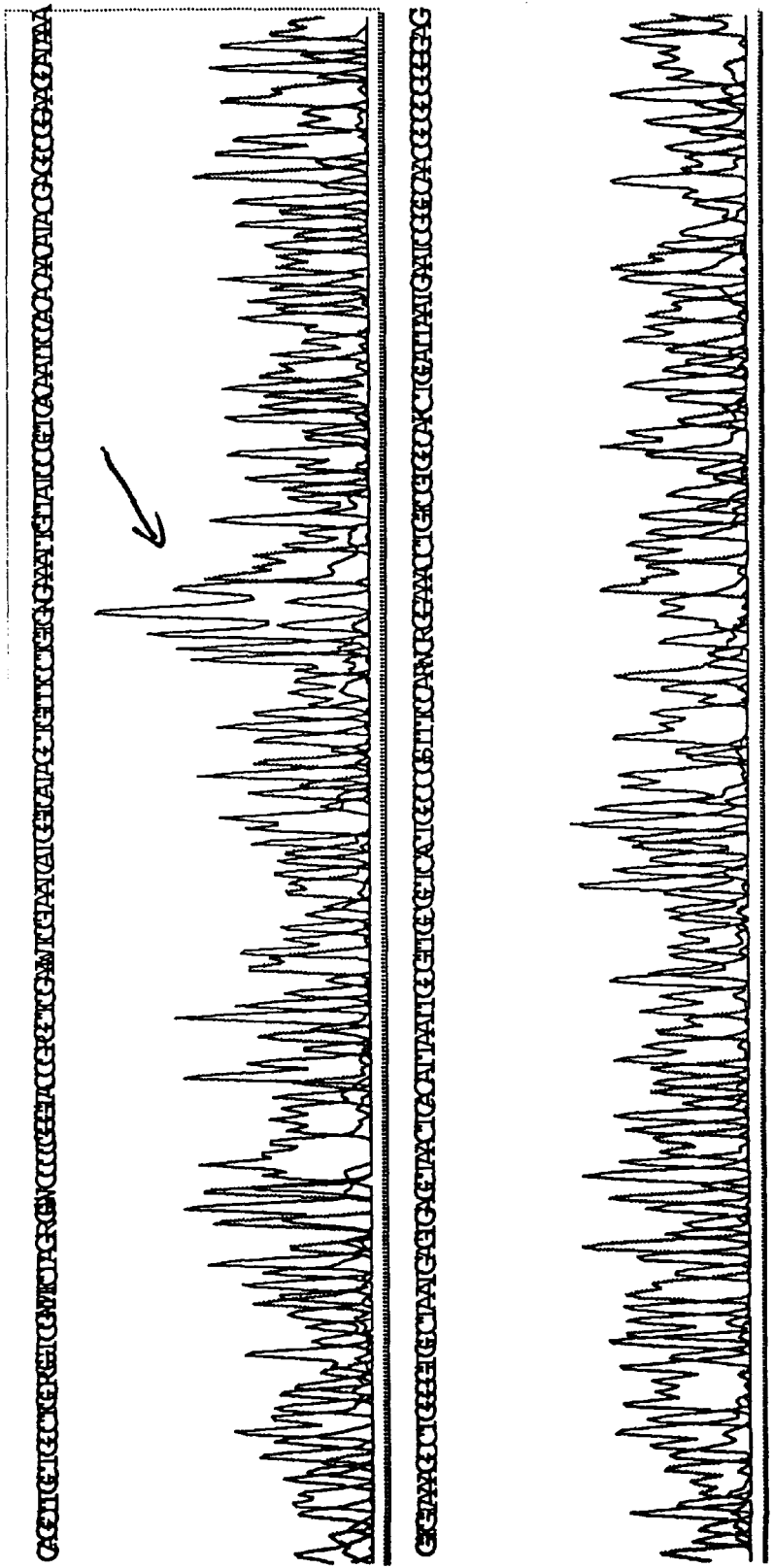
FIG. 10 depicts the results of an automated capillary electrophoresis sequencing run, wherein the polymerase extension product denaturing solution contained formamide, alkaline EDTA, and 5 mM DTT, and wherein the capillary electrophoresis was performed 15 hours after suspending the polymerase extension product in the denaturing solution. As compared to FIG. 7, reduced degradation of the polymerase extension products is evident.
Figure 10A:
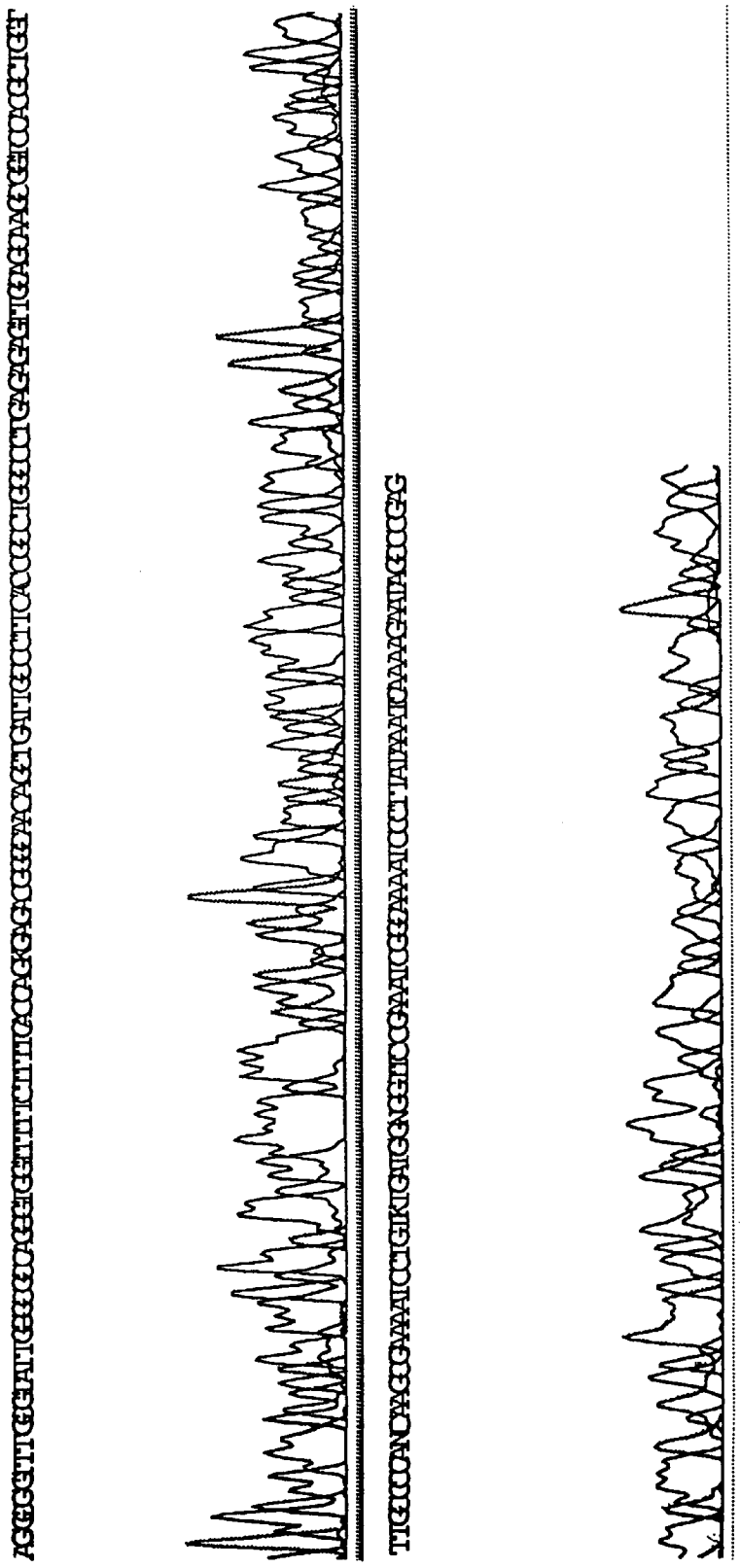

Nonlimiting examples of reducing agents which could be utilized in the present invention include β-mercaptoethanol, sodium metabisulfate, dithiothreitol (DTT), dithioerythreitol, and cysteine. A preferred reducing agent is β-mercaptoethanol, which is useful in any concentration up to about 0.5% (71 mM), for example at 0.01%, 0.05%, 0.1%, 0.2%, 0.3%, or 0.4%. When used at 0.5%, β-mercaptoethanol causes a somewhat reduced resolution of the data. A more preferred reducing agent is DTT, which is useful in concentrations as high as 10–20 mM or higher. Useful concentrations include any concentration between about 0.5 mM and 10 mM, for example 0.5 mM, 1 mM, 2.5 mM, 5 mM or 10 mM. Compare FIG. 7 (no DTT, 15 hours exposure to air) with FIG. 8 (1 mM DTT, 15 hours), FIG. 9 (2.5 mM DTT, 15 hours), FIG. 10 (5 mM DTT, 15 hours), and FIG. 11 (10 mM DTT, 15 hours). Electrophoretic resolution of the polymerase extension products is unaffected by DTT at these concentrations.

Figure 12:
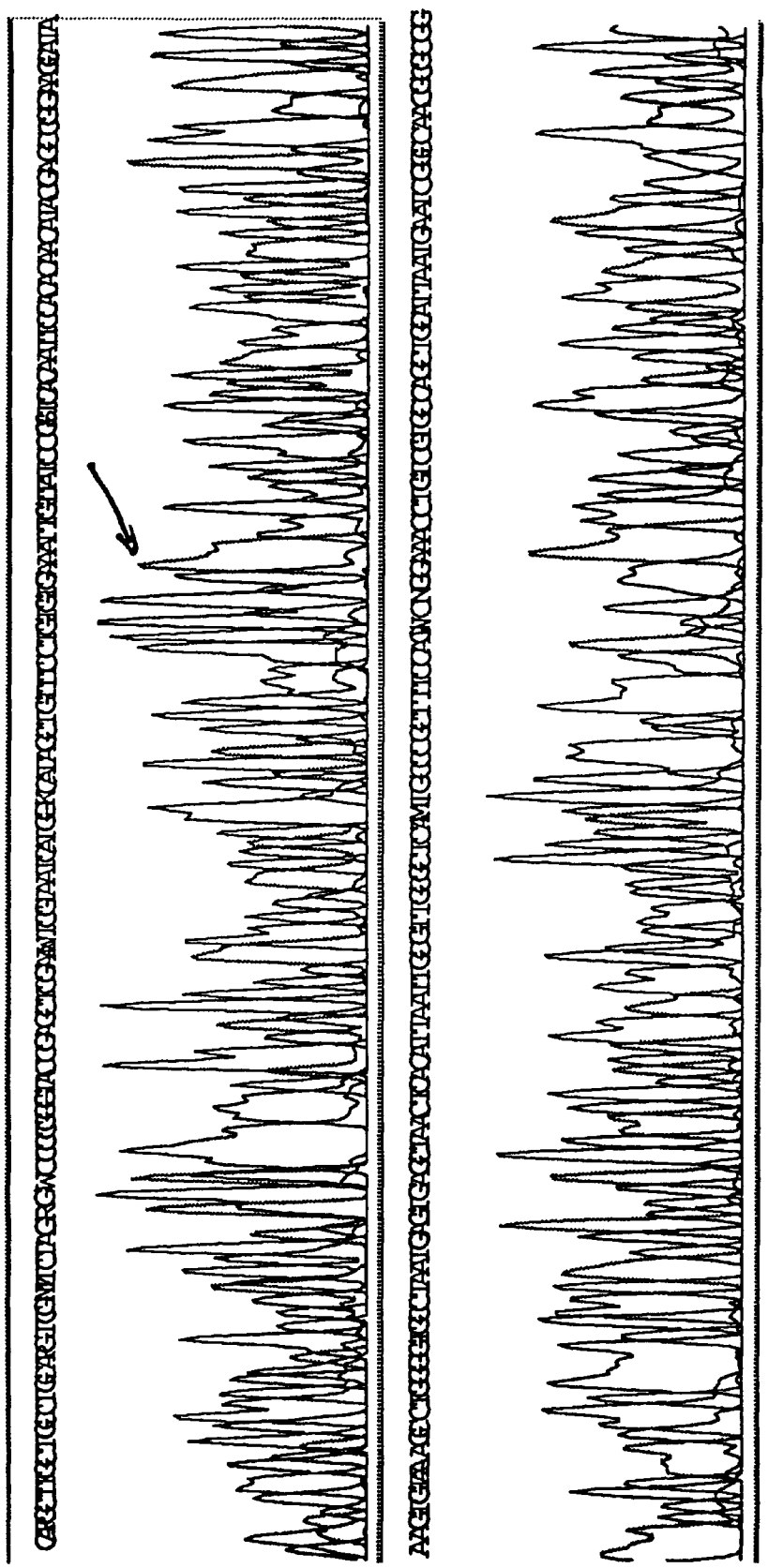
FIG. 12 depicts the results of an automated capillary electrophoresis sequencing run, wherein the polymerase extension product denaturing solution contained formamide, alkaline EDTA, 5 mM DTT, and 0.3 mM NaHCO$_3$, and wherein the capillary electrophoresis was performed 15 hours after suspending the polymerase extension product in the denaturing solution. No degradation of the polymerase extension products is evident.
Figure 12A:
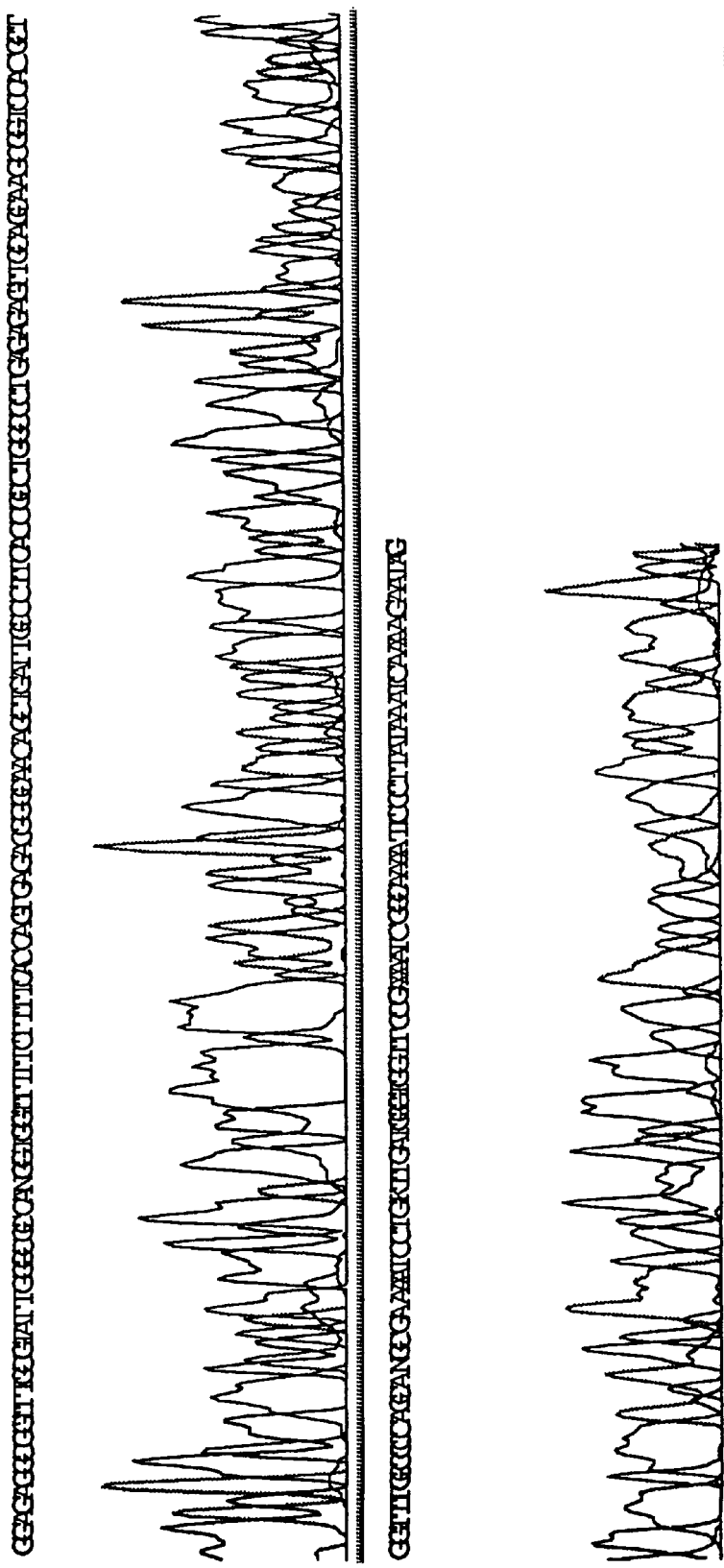
Figure 13:
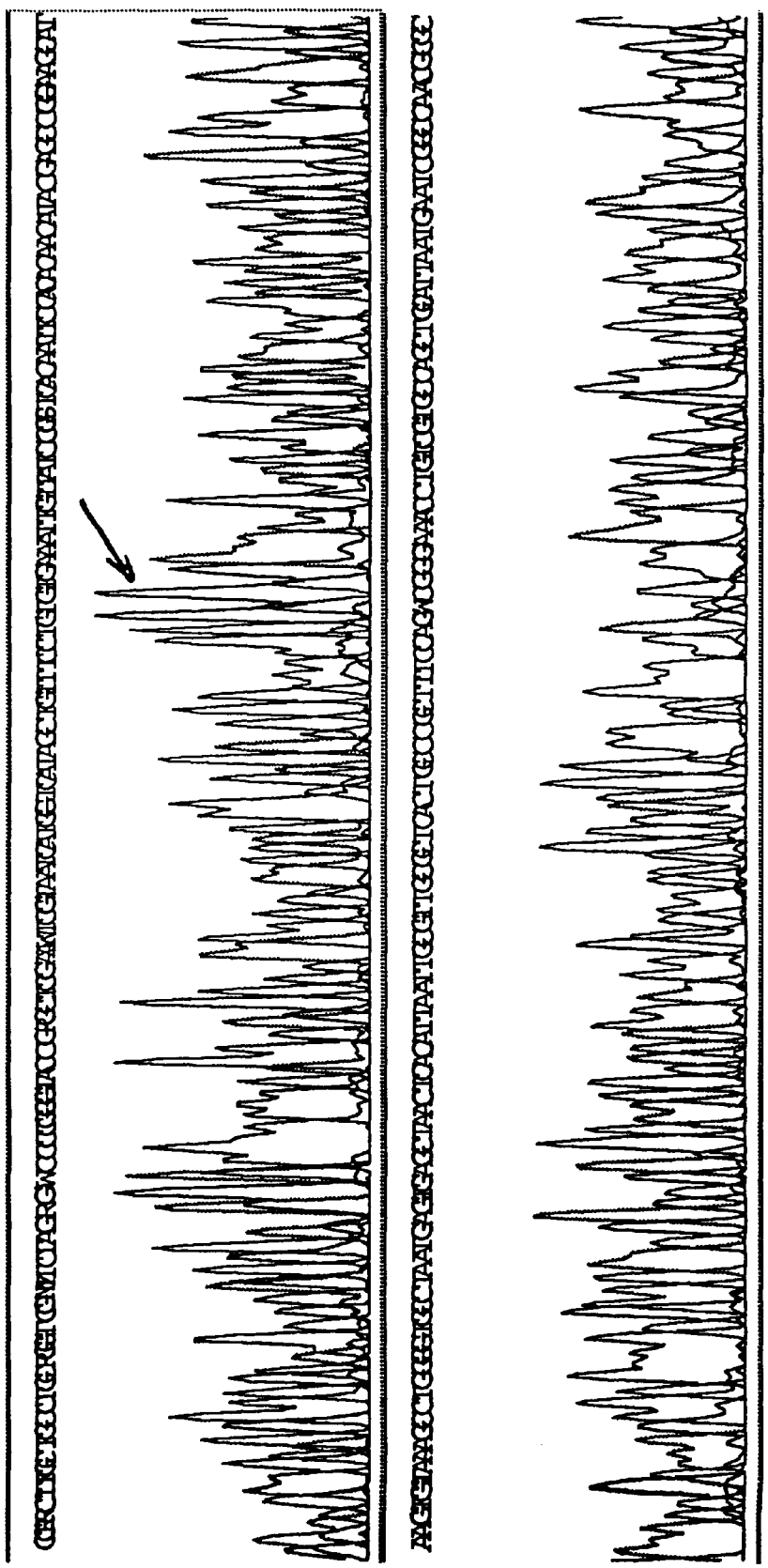
FIG. 13 depicts the results of an automated capillary electrophoresis sequencing run, wherein the polymerase extension product denaturing solution contained formamide, alkaline EDTA, 5 mM DTT, and 0.3 mM Tris pH 9.0, and wherein the capillary electrophoresis was performed 15 hours after suspending the polymerase extension product in the denaturing solution. No degradation of the polymerase extension products is evident.
Figure 13A:
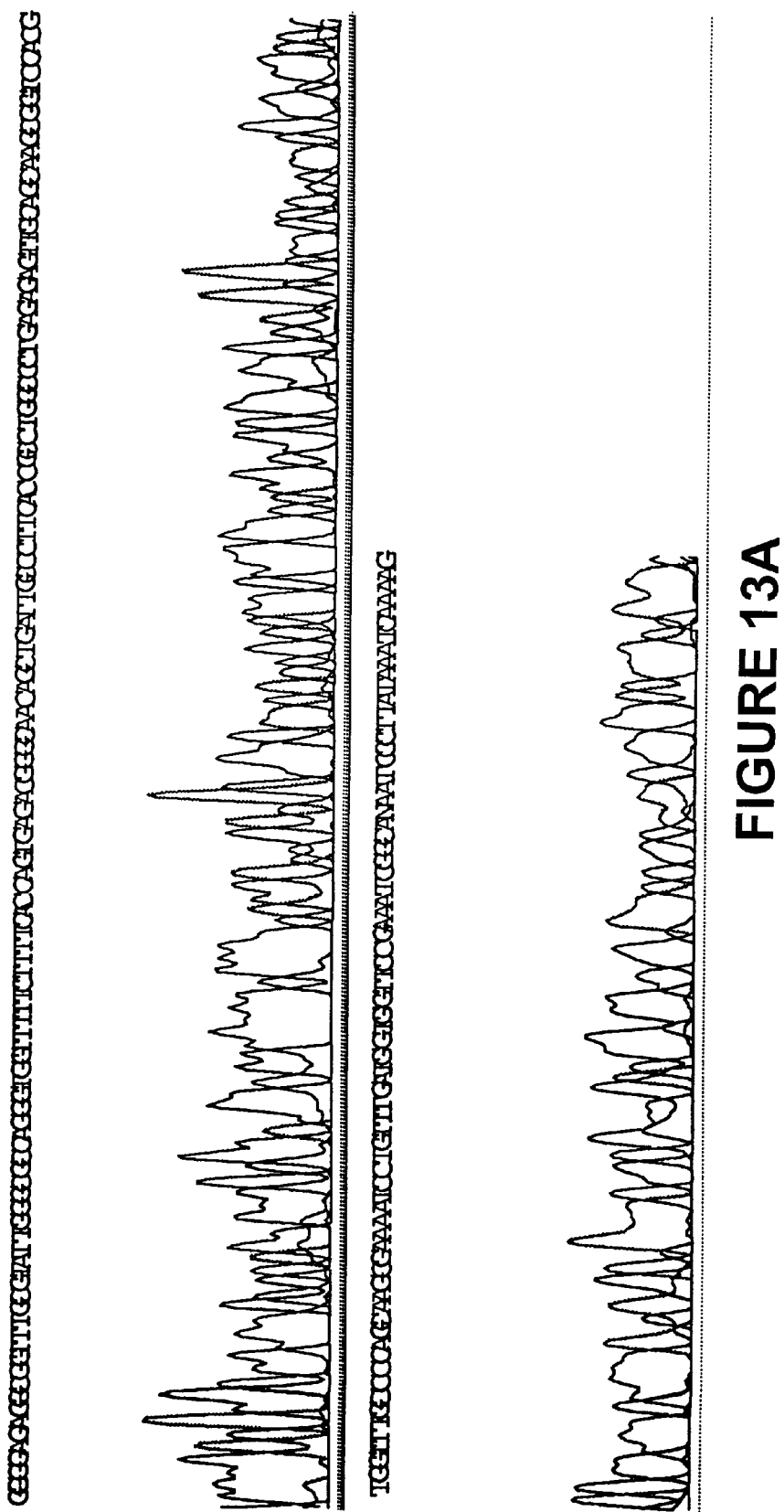
Figure 16:
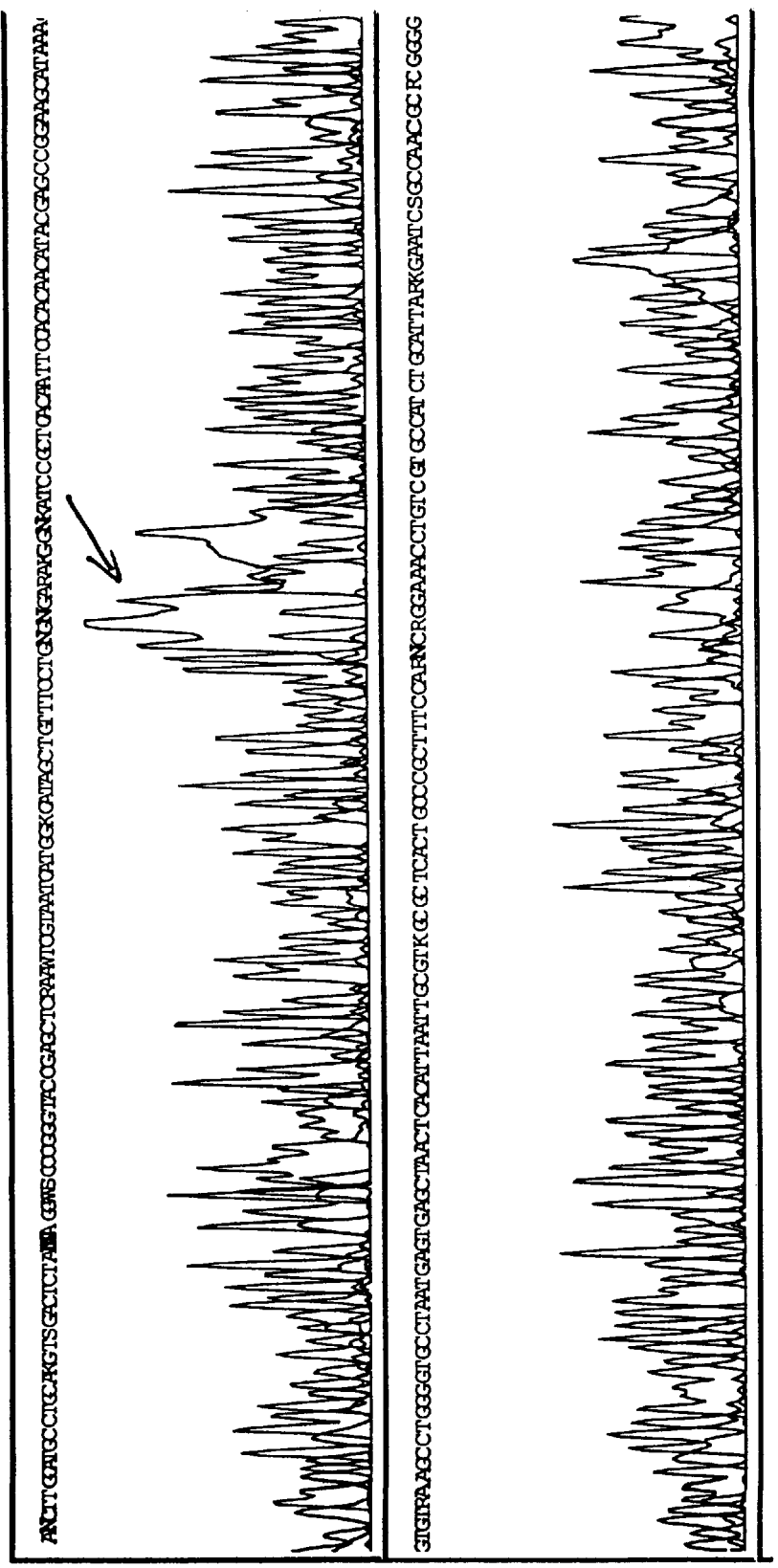
FIG. 16 depicts the results of an automated capillary electrophoresis sequencing run, wherein the polymerase extension product denaturing solution contained formamide, alkaline EDTA, and 0.3 mM Tris pH 9.0, and wherein the capillary electrophoresis was performed 15 hours after suspending the polymerase extension product in the denaturing solution. As compared to FIG. 7, reduced degradation of the polymerase extension products is evident.
Figure 16A:
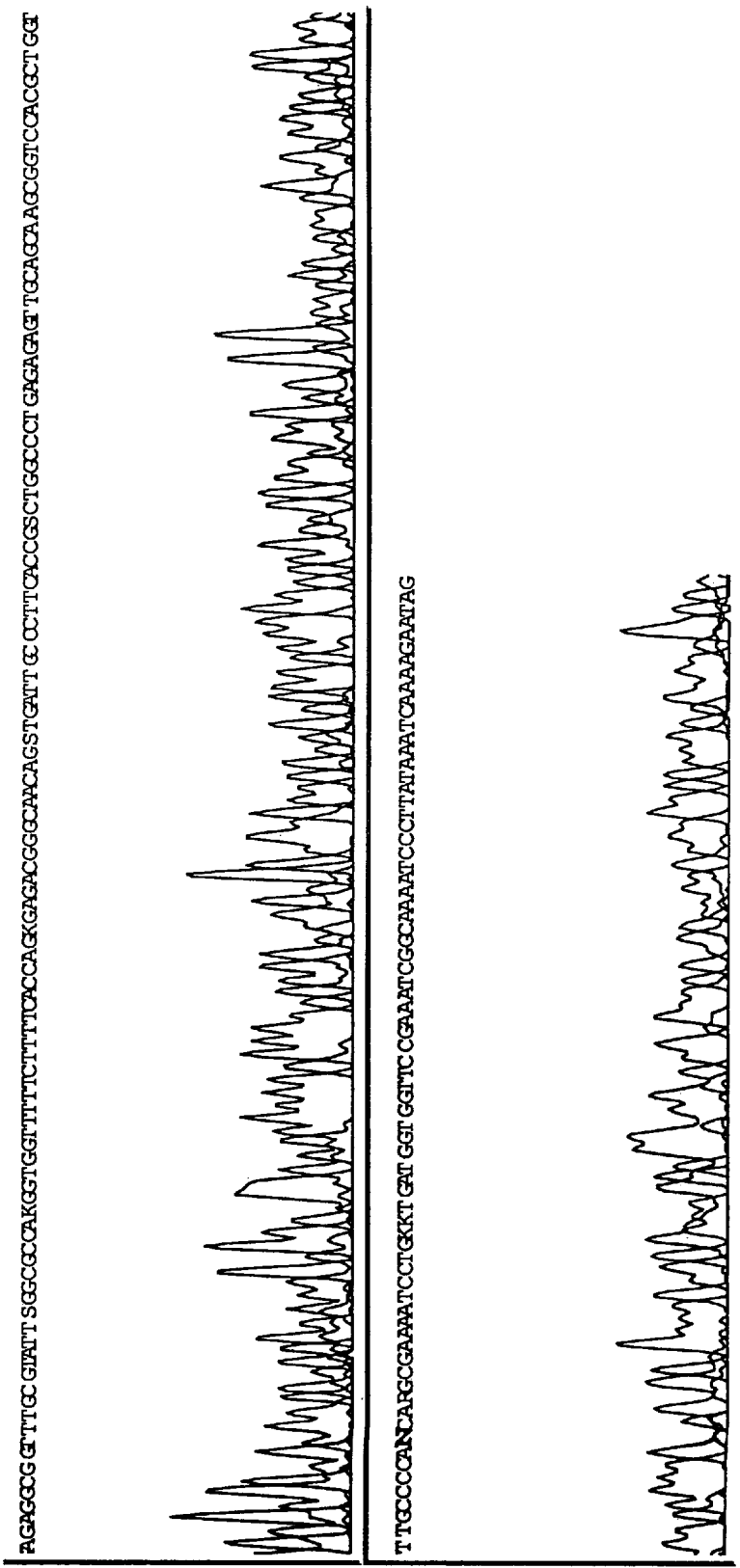

The effect of addition of base, buffer, or reducing agents on reducing degradation of polymerase extension products is additive. For example, sequencing reactions exposed to air for 15 hours in the presence of 5 mM DTT and 0.3 mM $NaHCO_3$ (FIG. 12) show greater stabilization than either component alone. A similar effect is seen with 0.3 mM Tris, pH 9.0 alone (FIG. 16, exposed for 15 hours) vs. 0.3 mM Tris, pH 9.0 with 5 mM DTT (FIG. 13).

Figure 14:
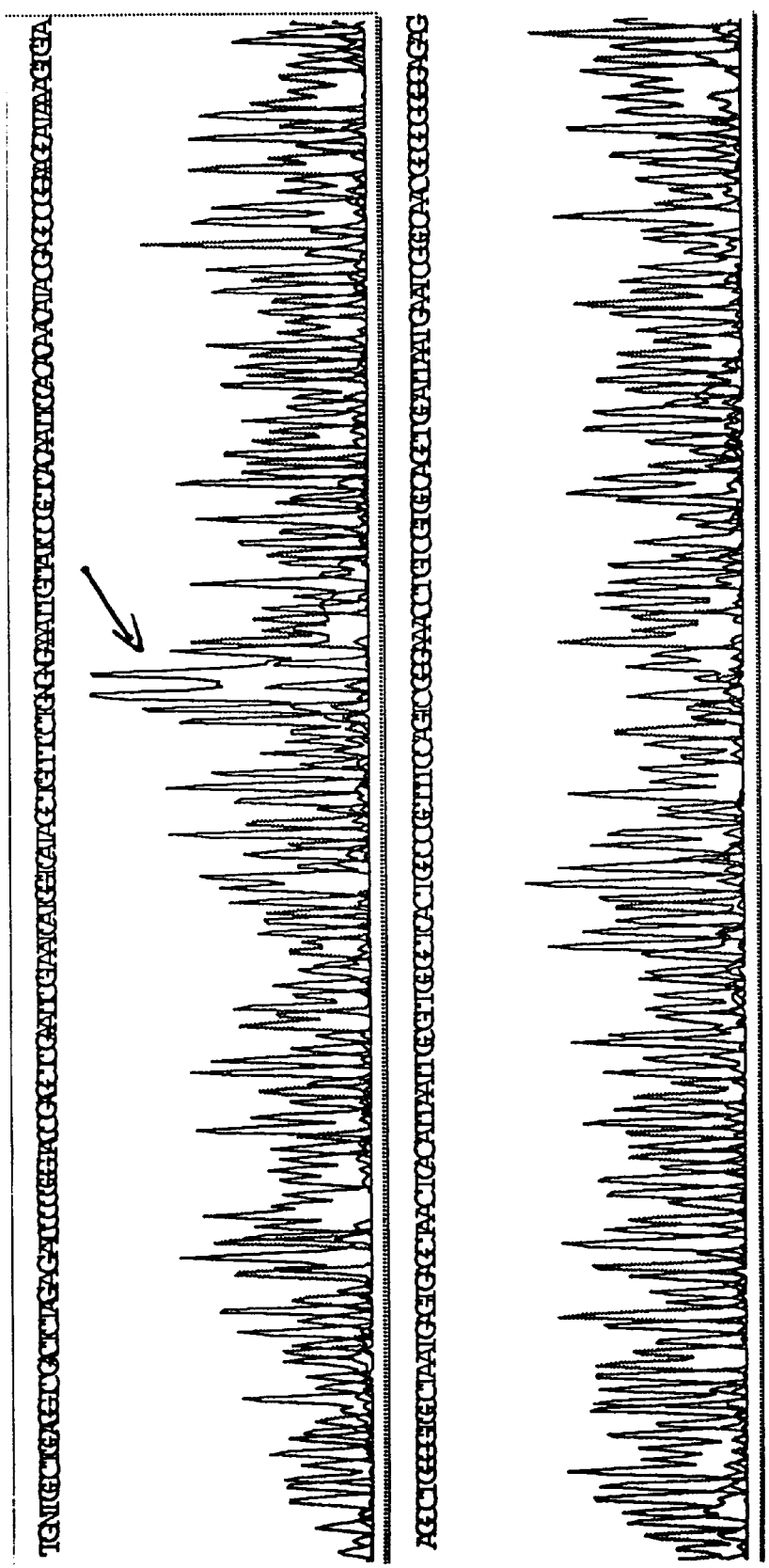
FIG. 14 depicts the results of an automated capillary electrophoresis sequencing run, wherein the polymerase extension product denaturing solution was covered with foil and contained formamide and alkaline EDTA, wherein the capillary electrophoresis was performed 32 hours after suspending the polymerase extension product in the denaturing solution. As compared to FIGS. 3 and 7, reduced degradation of the polymerase extension products is evident.
Figure 14A:
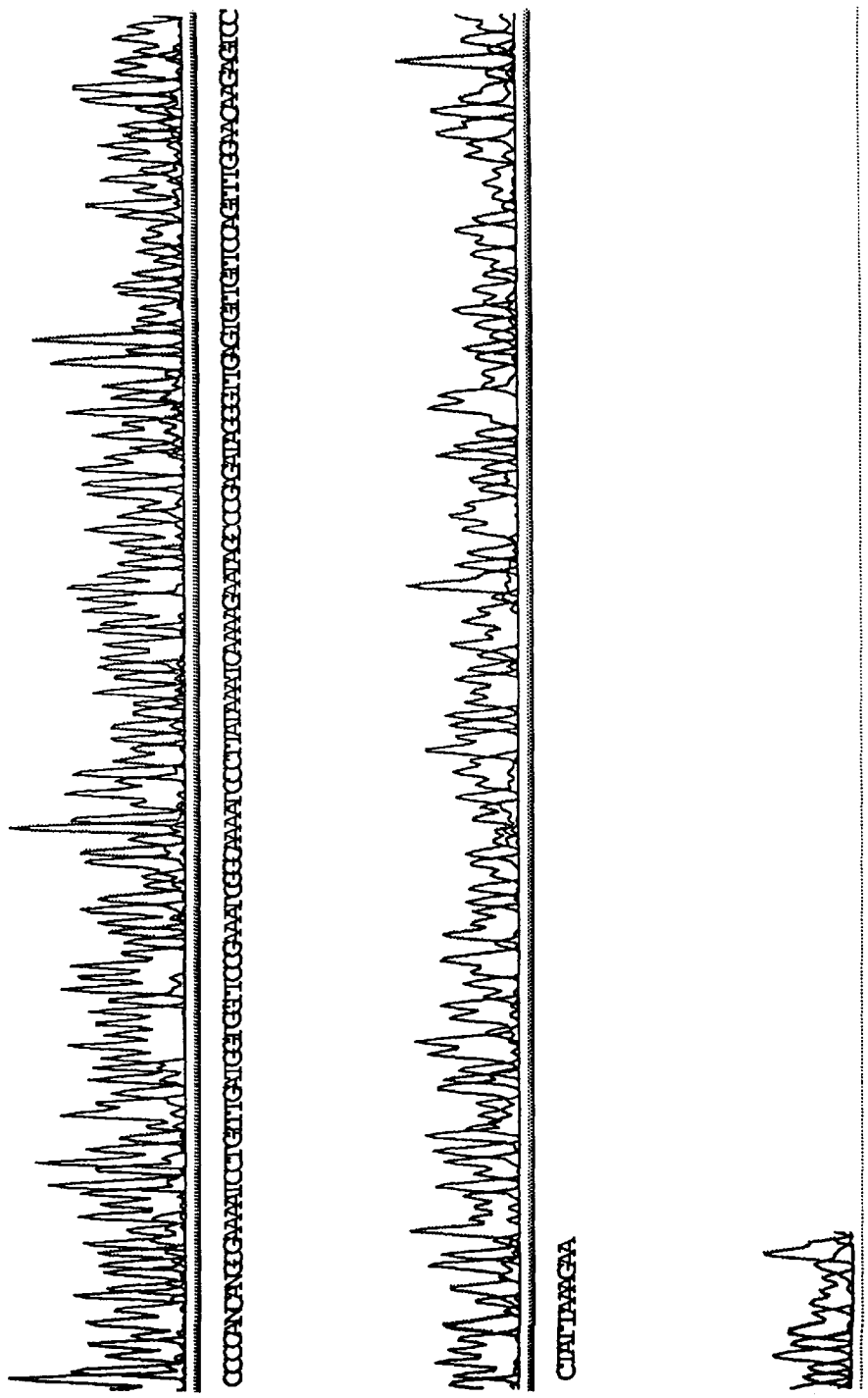

Covering the sequencing samples during incubation (e.g., with aluminum foil) is also useful for reducing degradation of polymerase extension products. Compare FIG. 14 (covered samples incubated at room temperature for 32 hours) with FIGS. 3 and 7 (uncovered samples incubated at room temperature for 21 and 15 hours, respectively). The most preferred treatment is foil covering and the addition of 10 mM DTT and 0.3 mM $NaHCO_3$, which stabilizes the covered samples so that they are completely protected even after 32 hours at room temperature. Another preferred treatment is foil covering with 5 mM DTT (without addition of base).

In other embodiments, the present invention is directed to methods for determining the sequence of a DNA template. The methods comprise:

(a) preparing a sequencing reaction mixture which comprises (i) the DNA template, (ii) a primer which is complementary to a 3' region of the DNA template, (iii) unlabeled deoxyribonucleoside triphosphates, (iv) at least one dideoxyribonucleoside triphosphate, (v) a DNA polymerase, (vi) a substance labeled with a fluorescent dye, wherein the substance is a deoxyribonucleoside triphosphate, the primer or the at least one dideoxyribonucleoside triphosphate; and (vii) an aqueous buffer;

(b) treating the sequencing reaction mixture under conditions and for a time sufficient to synthesize a series of polymerase extension products of different lengths, wherein each of the polymerase extension products comprises a sequence of nucleotides complementary to at least part of the DNA template and wherein at least one of the nucleotides in each extension product comprises the fluorescent dye;

(c) mixing the purified polymerase extension products with a denaturing solution comprising formamide, wherein the denaturing solution further comprises at least one compound that reduces degradation of the nucleotide comprising the fluorescent dye, wherein the at least one compound is not alkaline ethylenediaminetetraacetic acid (EDTA); and (d) analyzing the denatured polymerase extension products to determine the sequence of nucleotides in the DNA template. This analyzing step is generally performed by electrophoresis by methods known in the art.

These methods are particularly suited for automated sequencing procedures, such as with a PE Biosystems ABI Prism® 3700 DNA analyzer, an ABI 310 analyzer or an Amersham MegaBACE™ sequencer, which utilize capillary electrophoresis, or with the ABI™ 373 DNA sequencer or the ABI Prism 377 DNA sequencer, both of which utilize slab gel electrophoresis.

In additional embodiments, the present invention is directed to the mixture of purified polymerase extension products, formamide, and at least one compound of step (c) in the above-disclosed method, where the compound is a base, a buffer or a reducing agent as previously disclosed.

The present invention is also directed to a kit for practicing any of the above-disclosed methods. The kit comprises a base, a buffer, or a reducing agent as previously disclosed, along with instructions which direct the use of the compound to reduce or prevent degradation of the polymerase extension products. The kit can also comprise other components of any of the above methods, such as a polymerase, unlabeled and/or labeled dNTPs, unlabeled and/or labeled ddNTPs, unlabeled or labeled primers, an aqueous buffer, components required for polymerase activity, or any combinations of the above components.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

EXAMPLE

This example describes a characterization of the degradation of the G-signal in sequencing polymerase extension products comprising BigDye™-labeled terminating nucleotides which were electrophoresed in capillaries using the PE Biosystems ABI Prism® 3700 DNA Analyzer automated sequencing system.

M13 DNA sequencing reactions were used for all experiments. The reactions were prepared as in "ABI Prism® BigDye™ Terminator Cycle Sequencing Ready Reaction Kit, with AmpliTaq® DNA Polymerase, FS," 1998, Perkin-Elmer Corporation. To each well of a 384 well plate, the following was added:

| | |
|---|---|
| 2 ul | ABI BigDye mix (Perkin-Elmer) |
| 6 ul | 2.5X dilution buffer (400 mM Tris-HCl, 10 mM MgCl$_2$, pH 9.0) |
| 0.08 ul | M13-21 forward primer, TGTAAAACGACGGCCAGT (SEQ ID NO:2), 100 pm/ul (Gemini) |
| 11.52 ul | water |
| 0.4 ul | single stranded M13mp18 (SEQ ID NO:1), at 500 ng/ul (Bayou Biolabs) |

The reactions were cycled 40 times under the following conditions
96° C., 10 sec
50° C., 5 sec
60° C., 2 min
Repeat 40 cycles
Hold at 14° C.

The samples were purified over a sephadex G50 column, pooled and then ethanol precipitated twice. The 384 samples were pooled into a total of 20 tubes. The ethanol precipitated samples were resuspended in 0.6 ml of deionized formamide with 0.3 mM alkaline EDTA (Perkin-Elmer) with or without the addition of various additives. The M13 sequencing reactions were run on a PE Biosystems ABI Prism® 3700 DNA Analyzer (Perkin-Elmer) according to the manufacturer's protocol using POP6™ polymer, except that the electrophoresis temperature was 42° C. and the cuvette temperature was 30° C.

Figure 2:
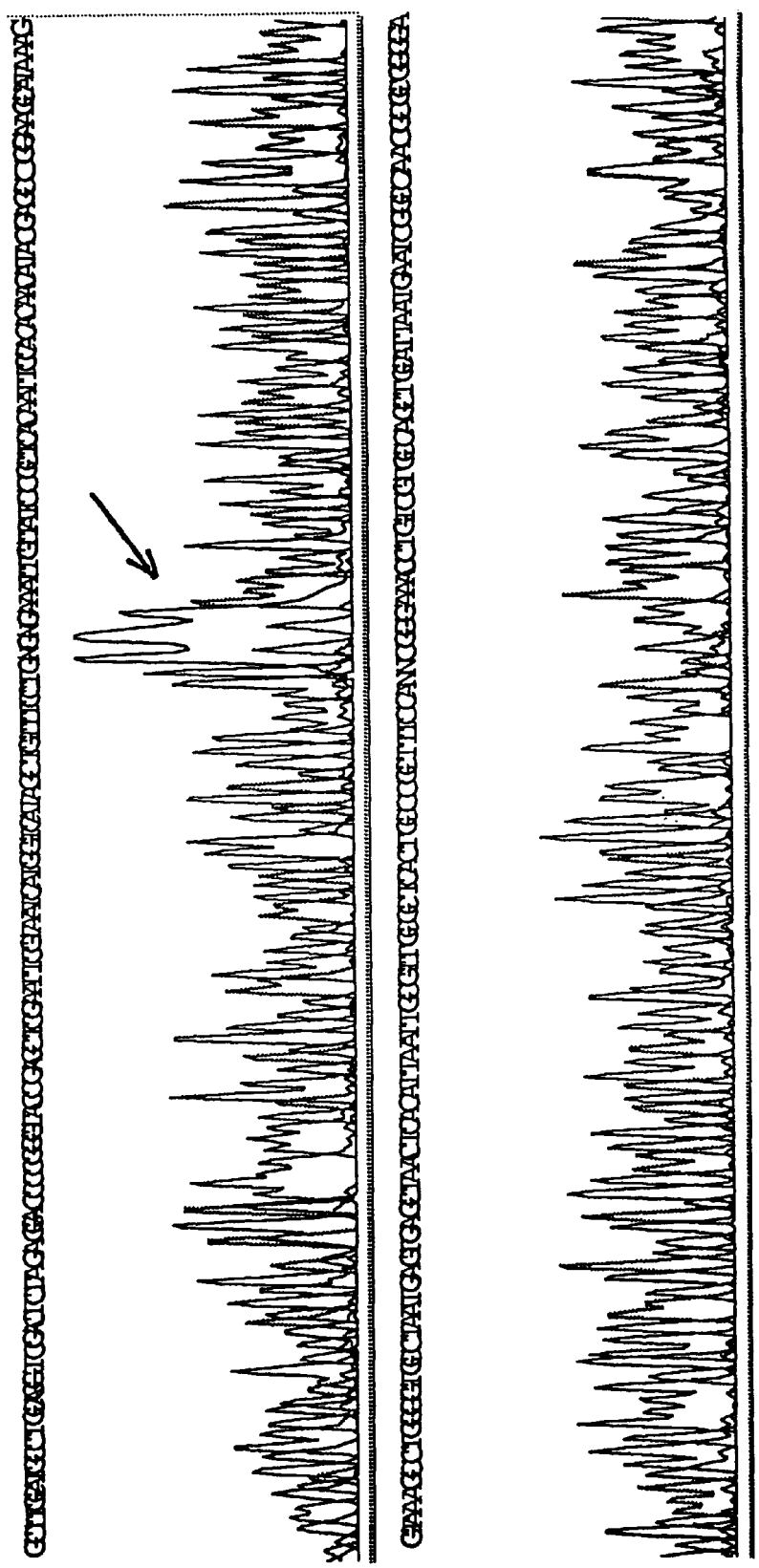
FIG. 2 depicts the results of an automated capillary electrophoresis sequencing run, wherein the polymerase extension product denaturing solution contained formamide, alkaline EDTA and 0.3 mM HCl, and wherein the capillary electrophoresis was performed immediately after suspending the polymerase extension product in the denaturing solution. As compared to the undegraded sample in FIG. 1, moderate degradation of the polymerase extension products is evident.
Figure 2A:
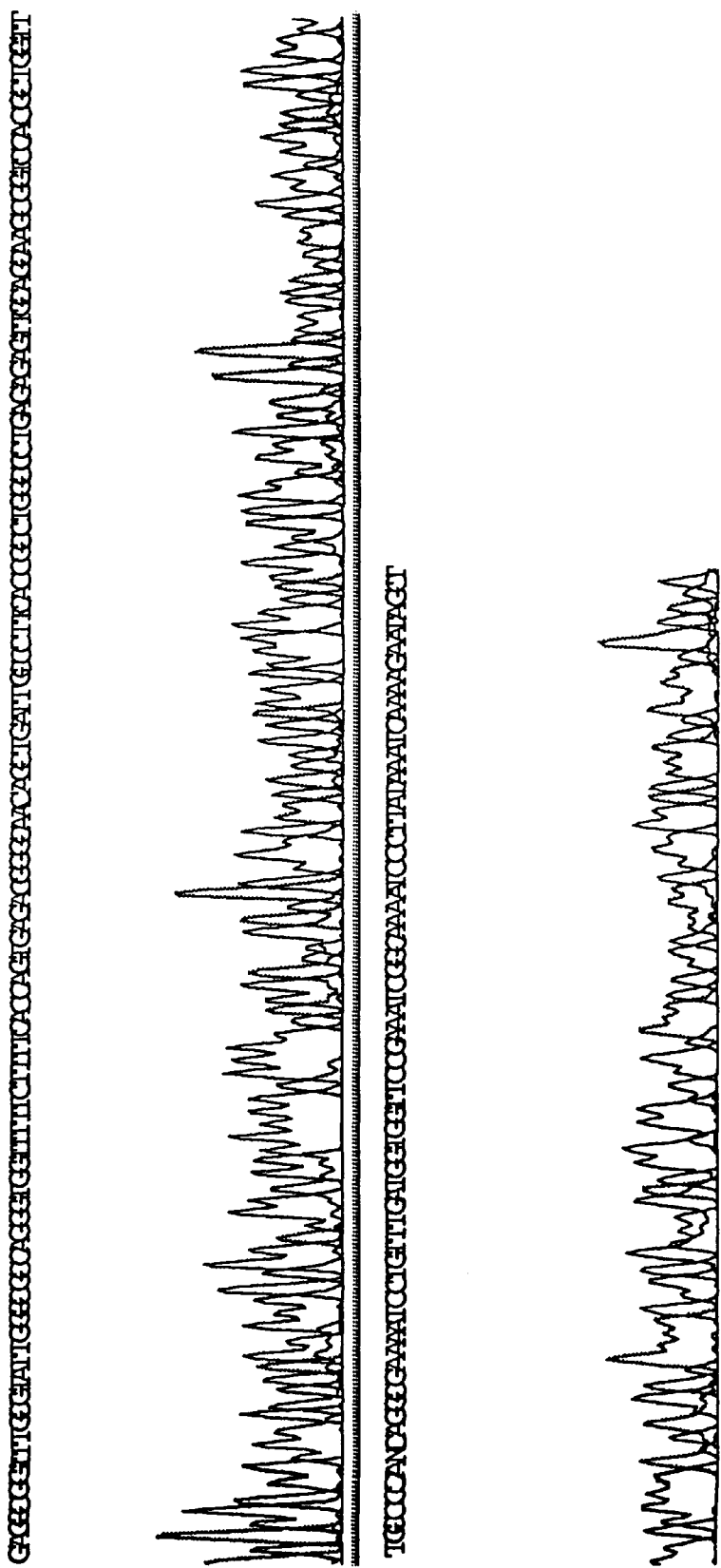
Figure 4:
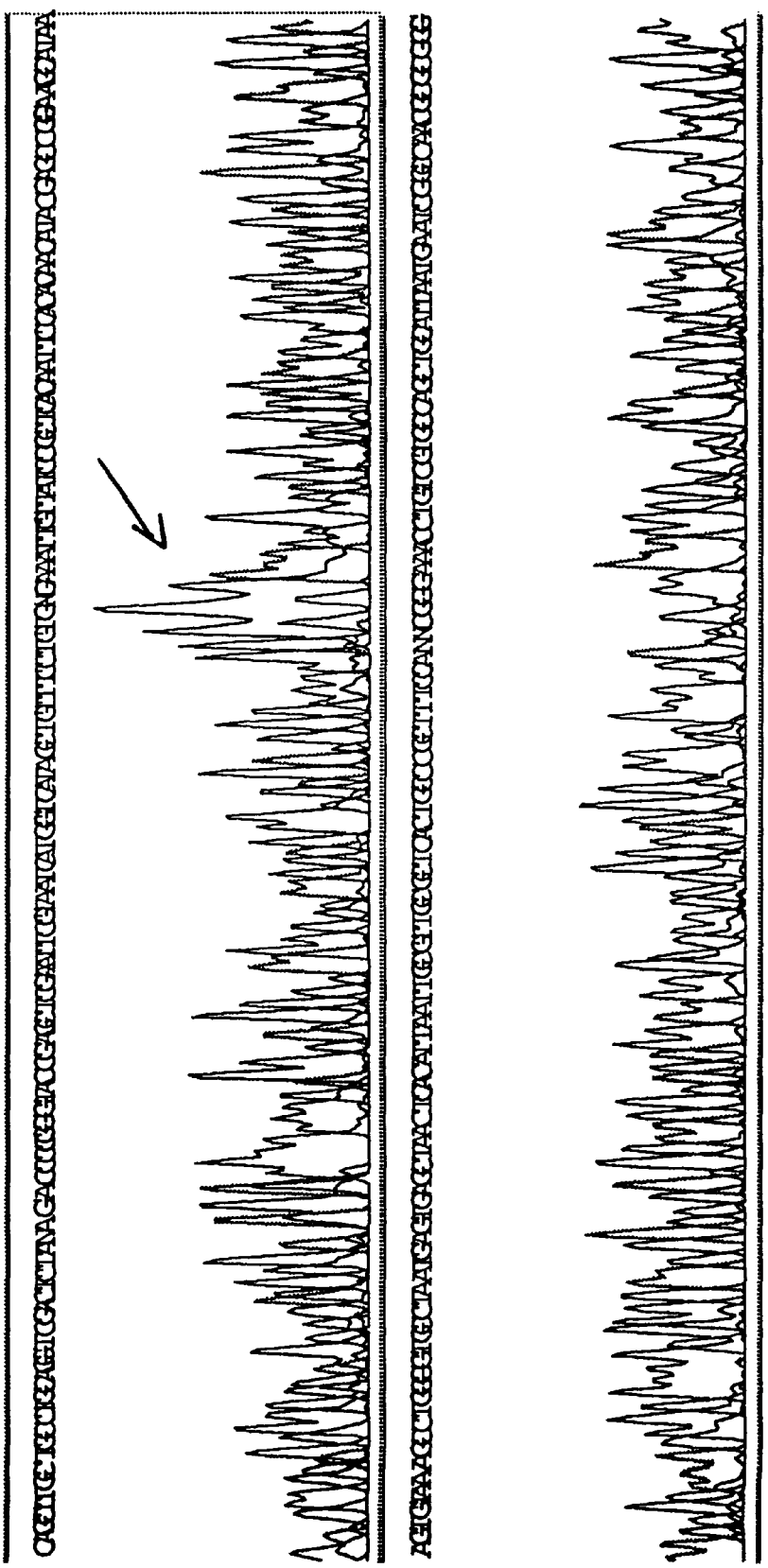
FIG. 4 depicts the results of an automated capillary electrophoresis sequencing run, wherein the polymerase extension product denaturing solution contained formamide, alkaline EDTA and 0.3 mM Tris pH 9.0, and wherein the capillary electrophoresis was performed 21 hours after suspending the polymerase extension product in the denaturing solution. As compared to FIG. 2, reduced degradation of the polymerase extension products is evident.
Figure 4A:
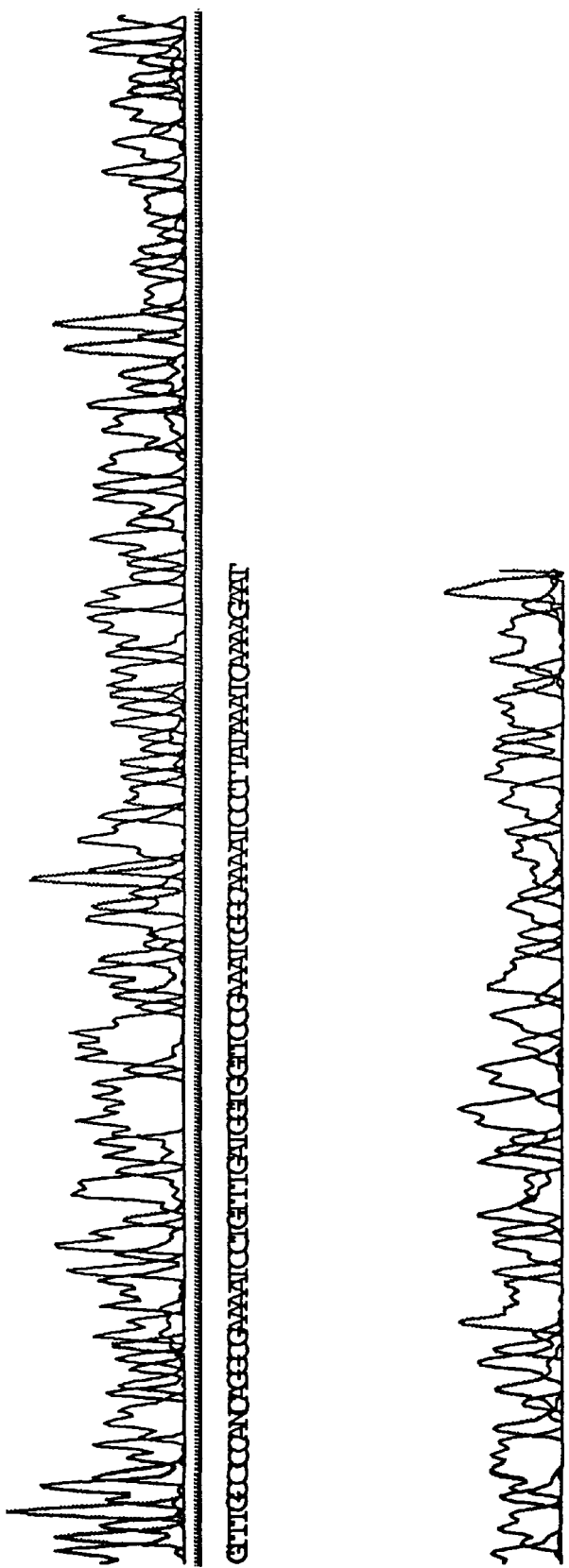
Figure 5:
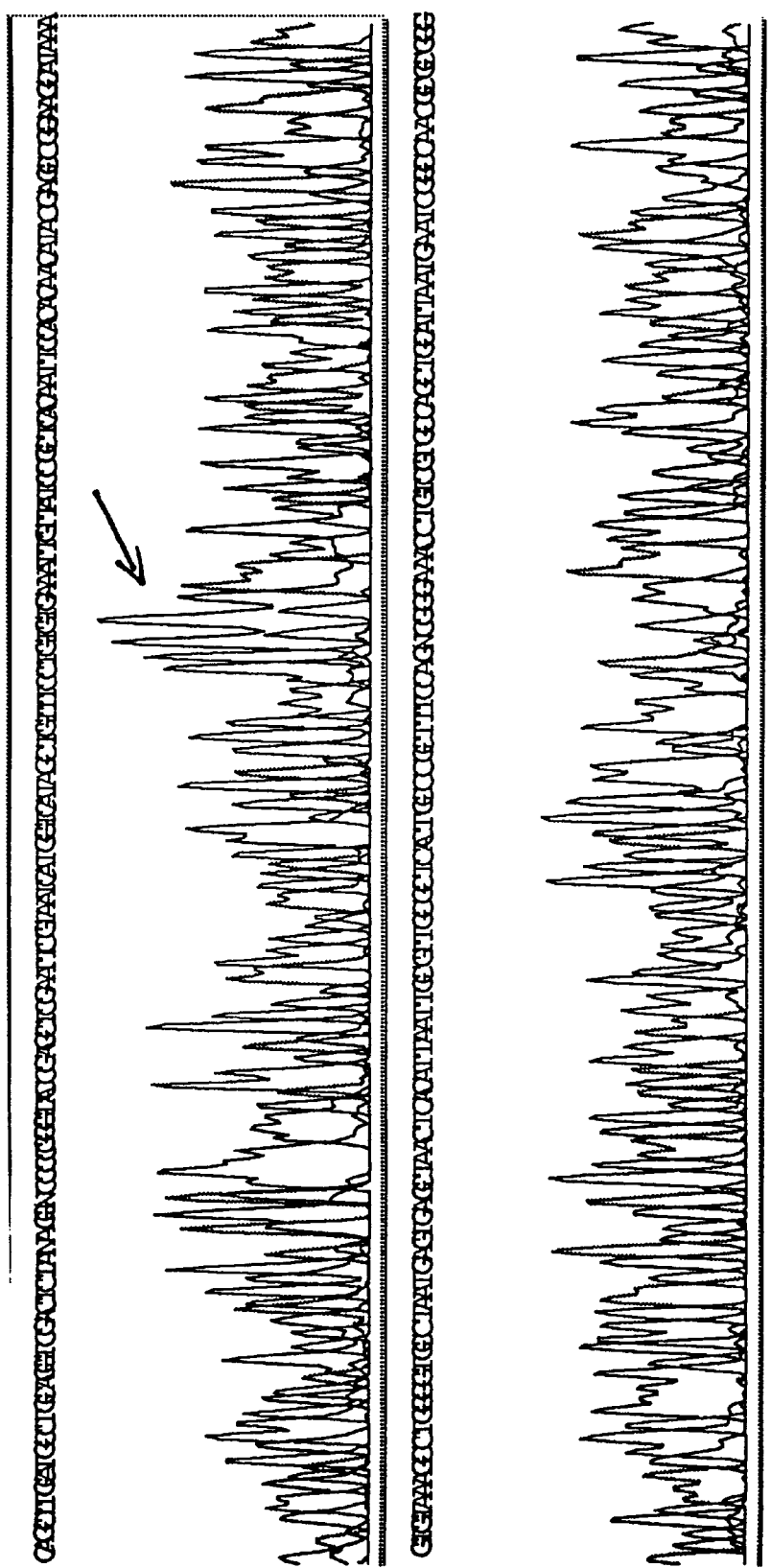
FIG. 5 depicts the results of an automated capillary electrophoresis sequencing run, wherein the polymerase extension product denaturing solution contained formamide, alkaline EDTA and 0.3 mM $NaHCO_3$, and wherein the capillary electrophoresis was performed 21 hours after suspending the polymerase extension product in the denaturing solution. As compared to FIG. 2, reduced degradation of the polymerase extension products is evident.
Figure 5A:
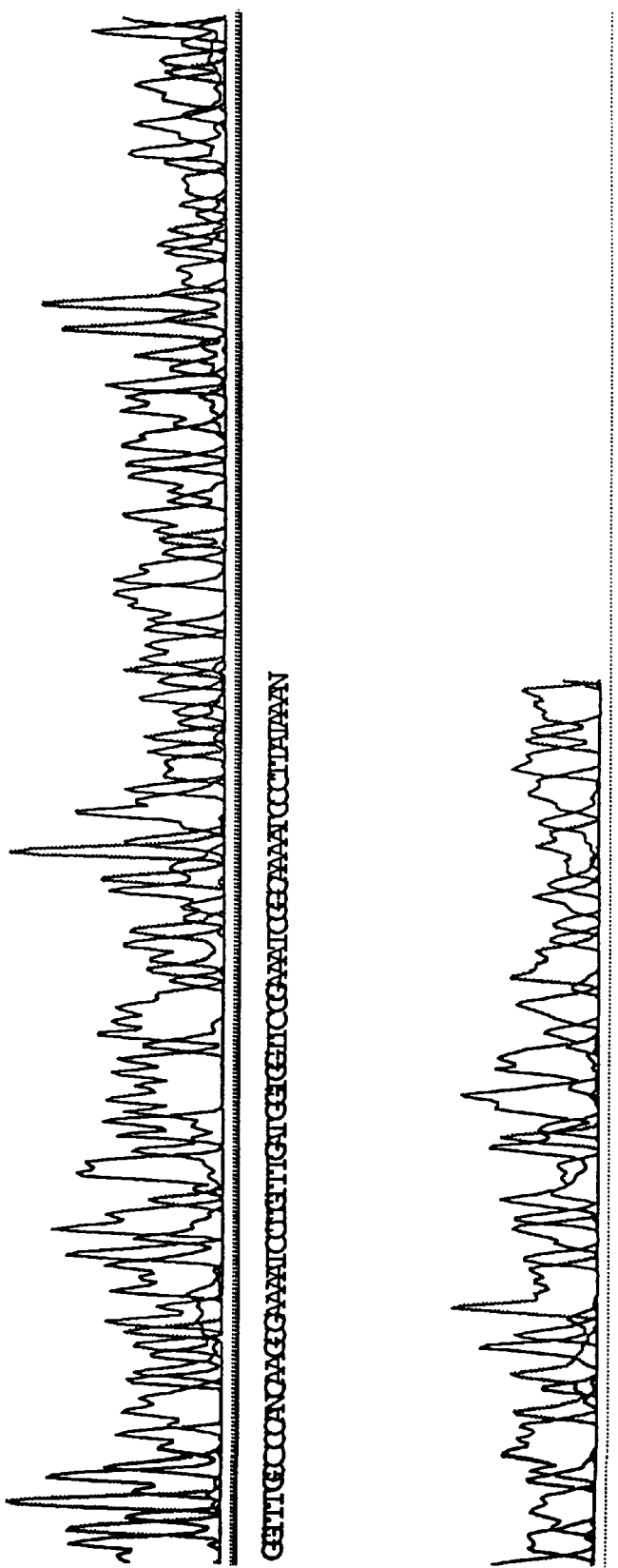

When the sequencing reaction was freshly resuspended in formamide without exposure to air and run on the 3700 DNA analyzer immediately (FIG. 1), no degradation of the polymerase extension products could be detected, since the polymerase extension products which terminate in all four bases could be consistently distinguished along the entire readable portion of the electrophoresis run, and there was no nonspecific concentration of dye anywhere along the run. However, samples that were exposed to air at room temperature showed a progressive degradation in sequence quality (FIG. 3, exposed for 21 hours). This was seen as excessive concentration of fluorescence at the wavelength of the G dye which comigrates with polymerase extension products which are about 90 nucleotides long. There was also reduced fluorescence of the G-terminated polymerase extension products. The reduction in fluorescence was sometimes so severe that the signal for the G-terminated products was almost completely destroyed, as in FIG. 7, where the polymerase extension products were exposed to air for 15 hr. This degradation was affected by the pH of the loading solution, as addition of HCl to 0.3 mM increased the amount of degradation, as in FIG. 2, where the polymerase extension products were not exposed to air. Addition of buffer Tris, pH 9.0, to 0.3 mM significantly stabilized the G reactions (FIG. 4, 21 hr exposure). Also, addition of base NaHCO$_3$ to 0.3 mM significantly stabilized the G reactions (FIG. 5, 21 hr exposure). The addition of NaHCO$_3$ raised the pH of the load solution from about 5.0 to about 5.5, as determined using pH paper.

Figure 6:
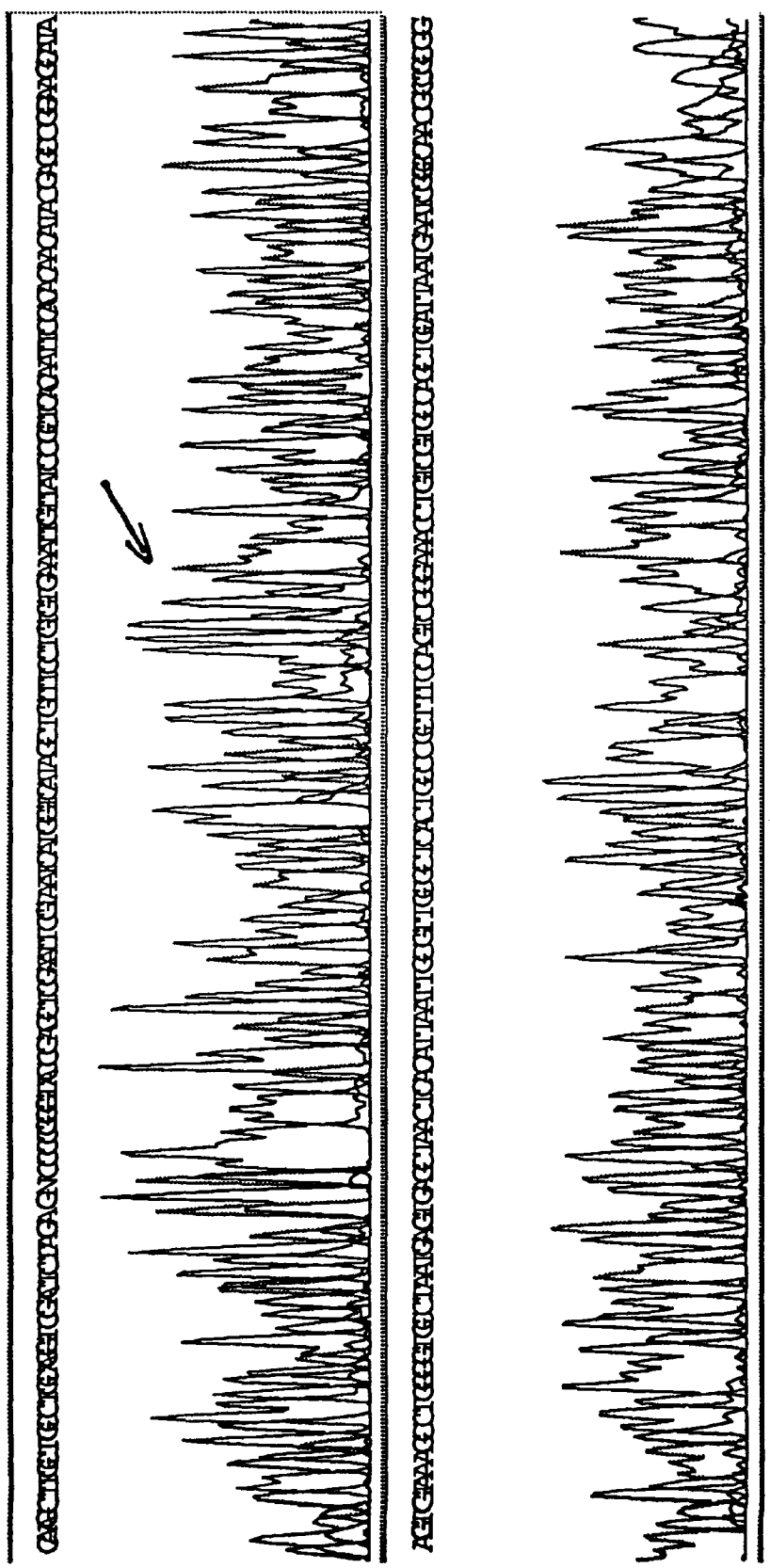
FIG. 6 depicts the results of an automated capillary electrophoresis sequencing run, wherein the polymerase extension product denaturing solution contained formamide, alkaline EDTA and 0.5% β-mercaptoethanol, and wherein the capillary electrophoresis was performed 21 hours after suspending the polymerase extension product in the denaturing solution. No degradation of the polymerase extension products is evident.
Figure 6A:
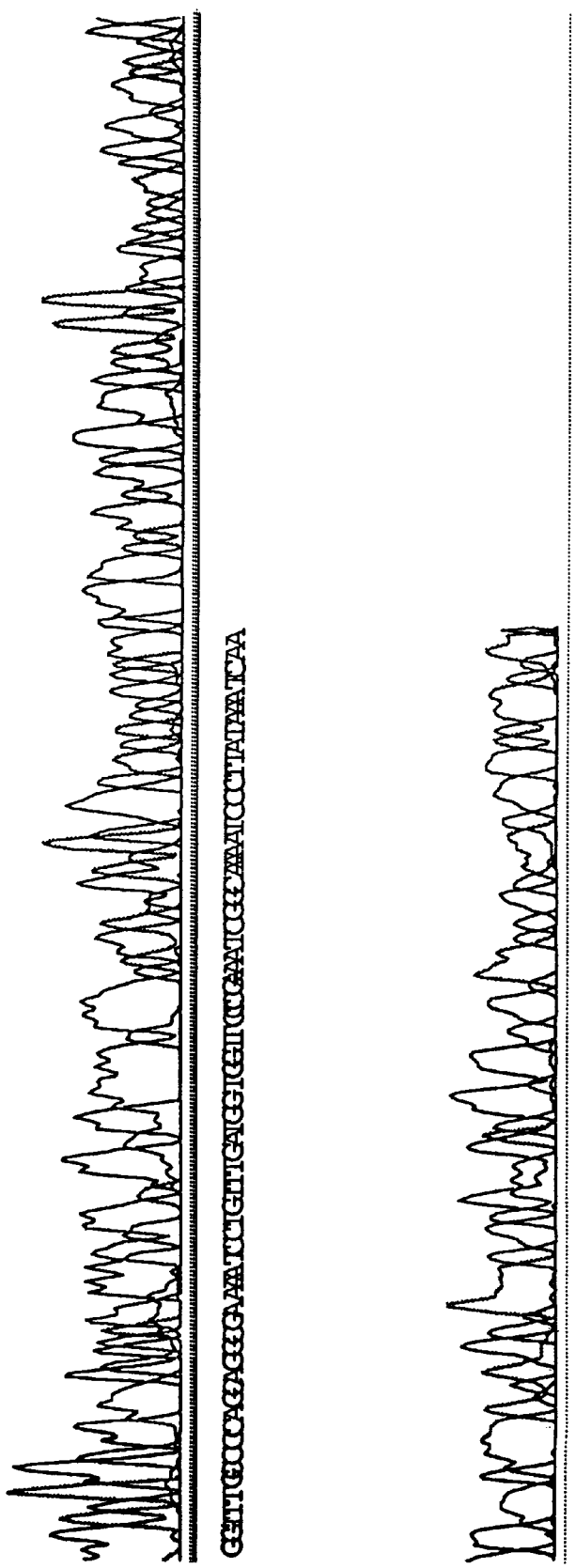
Figure 11:
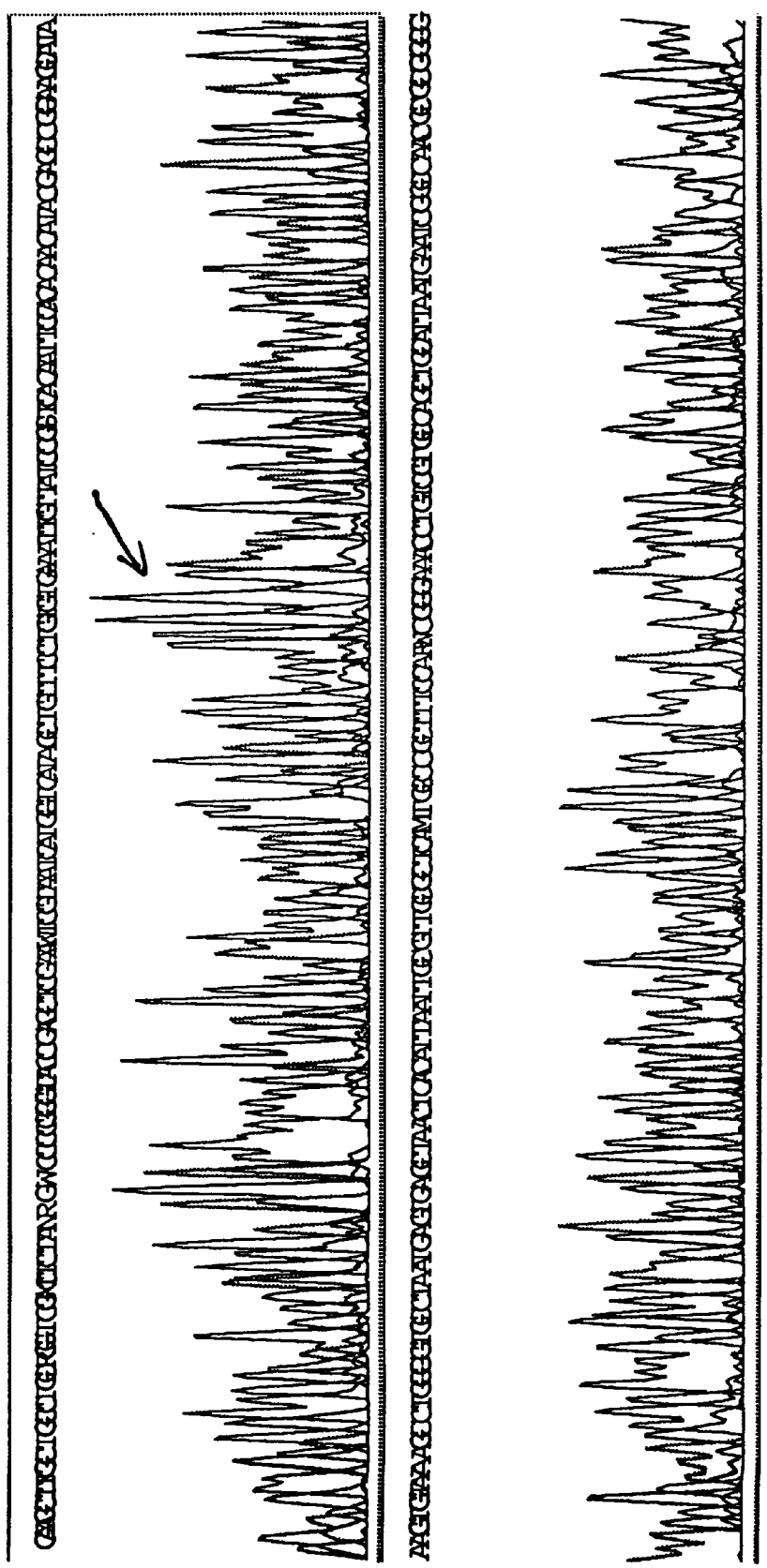
FIG. 11 depicts the results of an automated capillary electrophoresis sequencing run, wherein the polymerase extension product denaturing solution contained formamide, alkaline EDTA, and 10 mM DTT, and wherein the capillary electrophoresis was performed 15 hours after suspending the polymerase extension product in the denaturing solution. No degradation of the polymerase extension products is evident.
Figure 11A:
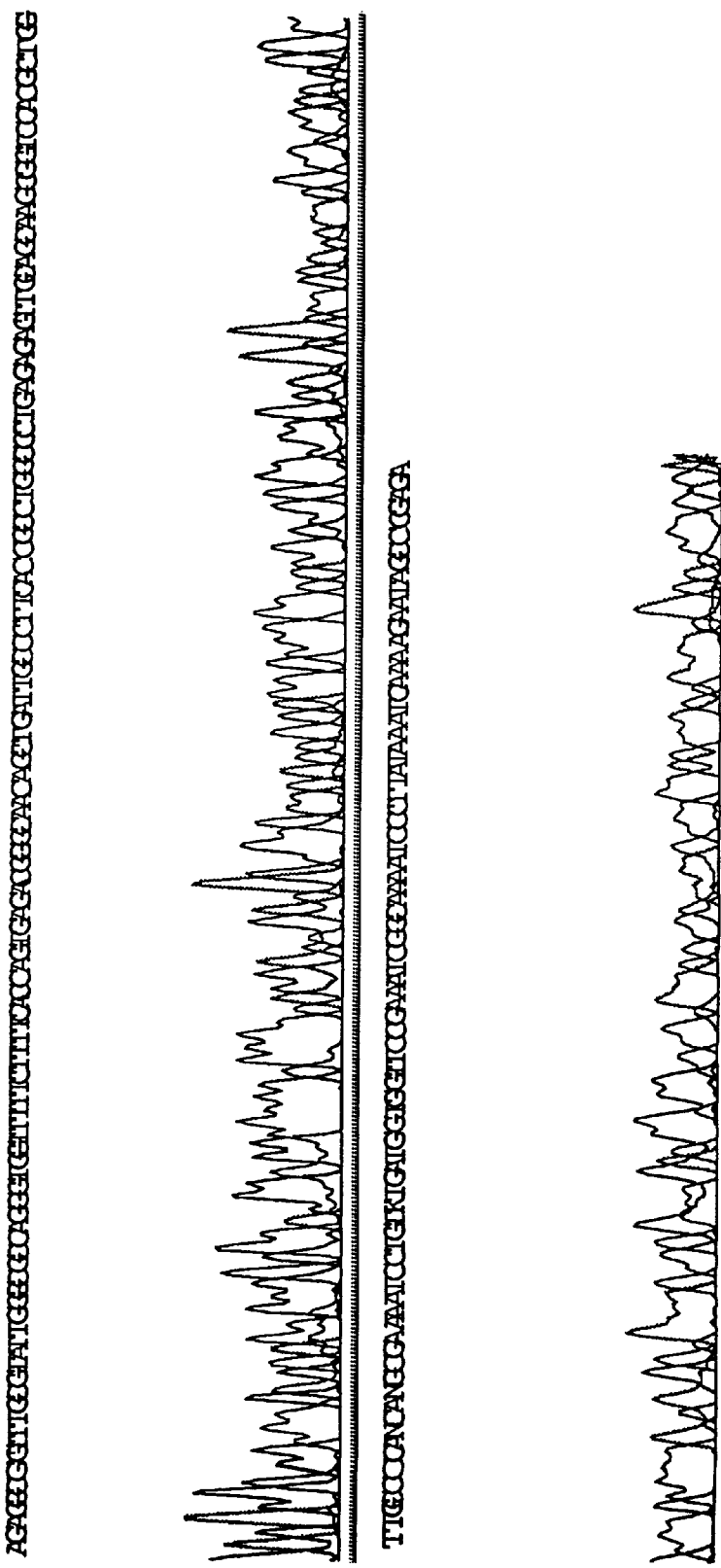

Reducing agents also increased the stability of the G reaction products. In FIG. 6 (21 hr exposure to air), addition of β-mercaptoethanol to 0.5% (71 mMol/l) eliminated the degradation of the G reaction products. However, resolution was somewhat reduced with all of the polymerase extension products. Dithiothreitol (DTT) had a similar effect, as seen by the increasing protection at 15 hours exposure as the amount of DTT is increased from 0 mM (FIG. 7), 1 mM (FIG. 8), 2.5 mM (FIG. 9), 5 mM (FIG. 10) and 10 mM (FIG. 11). Resolution was unaffected by these concentrations of DTT.

The effect of addition of base and reducing agents was additive. Reactions exposed to air for 15 hours in the presence of 5 mM DTT and 0.3 mM NaHCO$_3$ (FIG. 12) showed a greater stabilization than either component alone. A similar effect was seen with 0.3 mM Tris, pH 9.0 alone (FIG. 16, exposed for 15 hours) and 0.3 mM Tris, pH 9.0 with 5 mM DTT (FIG. 13).

Figure 15:
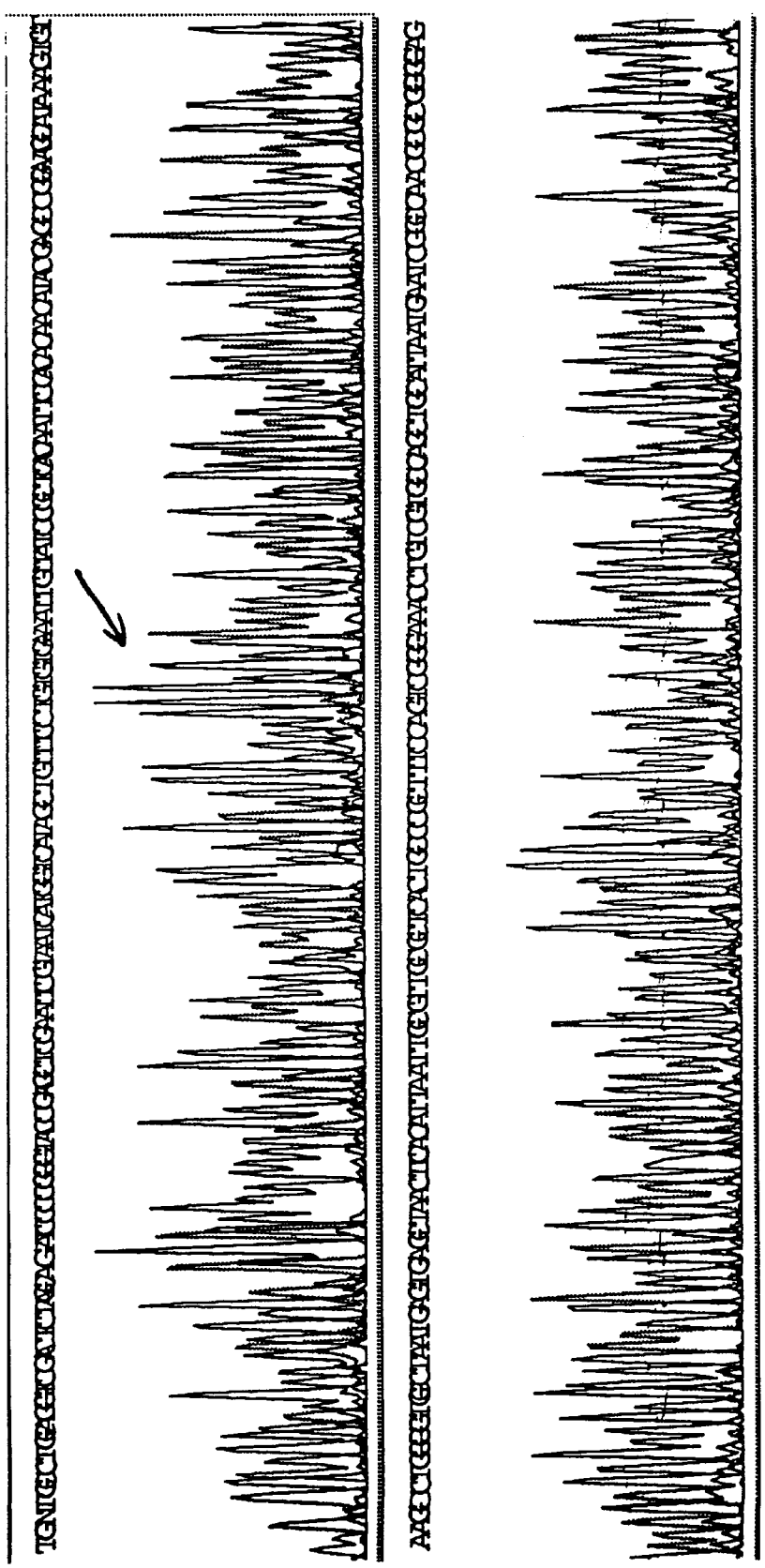
FIG. 15 depicts the results of an automated capillary electrophoresis sequencing run, wherein the polymerase extension product denaturing solution was covered with foil and contained formamide, alkaline EDTA, 10 mM DTT, and 0.3 mM NaHCO$_3$, and wherein the capillary electrophoresis was performed 32 hours after suspending the polymerase extension product in the denaturing solution. No degradation of the polymerase extension products is evident.
Figure 15A:
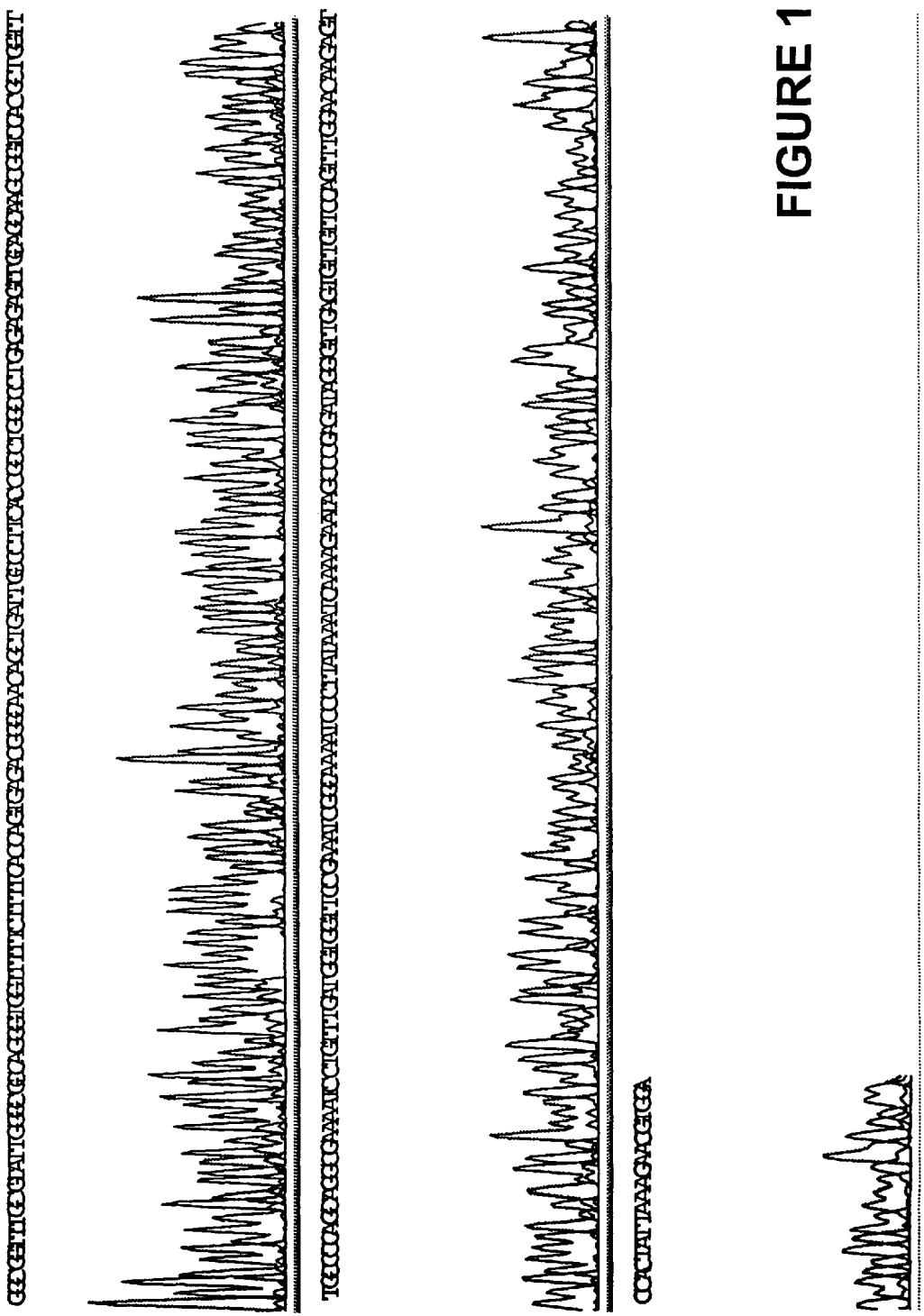

Covering the sequencing samples prior to loading stabilized the sequencing samples. See FIG. 14, covered samples incubated at room temperature for 32 hours, compared with FIGS. 3 and 7, 21 hours and 15 hours, respectively. Addition of 10 mM DTT and 0.3 mM NaHCO$_3$ further stabilized the covered samples, which showed no degradation after 32 hours at room temperature (FIG. 15).

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

TABLE 1
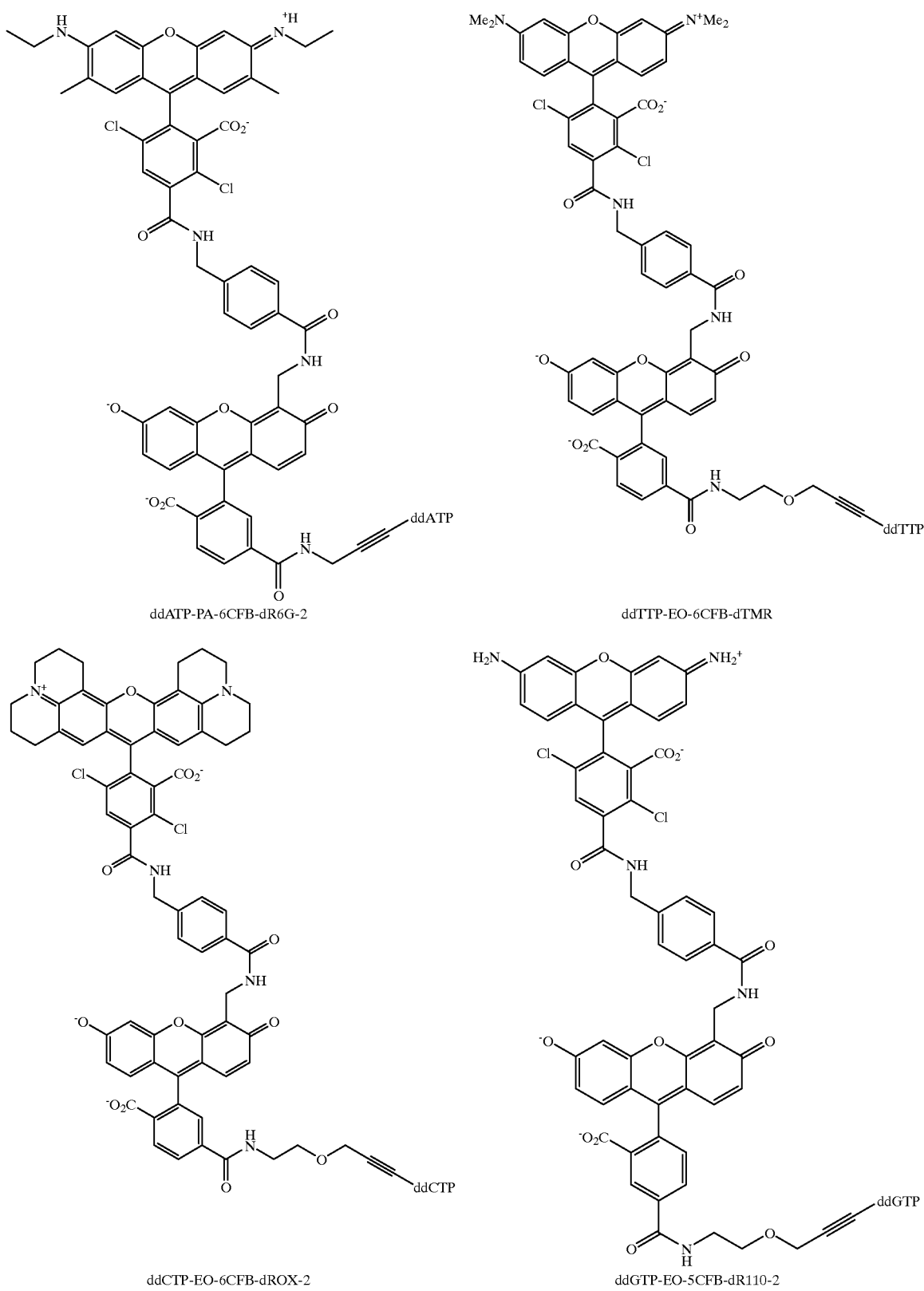

What is claimed is:

1. A method of reducing degradation of fluorescent dye-labeled polymerase extension products, comprising adding to the extension products formamide and at least one additional compound selected from the group consisting of a base, a buffer and a reducing agent, wherein the additional compound is not alkaline ethylenediaminetetraacetic acid (EDTA), and wherein less degradation of polymerase extension products occurs in the presence of formamide and the additional compound a in the presence of formamide without the additional compound.

2. The method of claim 1, wherein the at least one compound is dithiothreitol (DTT).

3. The method of claim 2, wherein the method further comprises adding $NaHCO_3$.

4. The method of claim 1, wherein the fluorescent dye is a fluorescent energy transfer dye.

5. The method of claim 4, wherein the fluorescent energy transfer dye is 5CFB-dR110-2.

6. The method of claim 4, wherein the at least one compound is DTT and the method further comprises adding $NaHCO_3$.

7. The method of claim 4, wherein the polymerase extension products terminate in four different dideoxyribonucleotides and at least one of the dideoxyribonucleotides is labeled with the fluorescent energy transfer dye.

8. The method of claim 7, wherein the at least one labeled dideoxyribonucleotide is ddG-EO-5CFB-dR110-2.

9. The method of claim 8, wherein addition of the compound prevents excessive fluorescence at about 530 nm, wherein the excessive fluorescence migrates in polyacrylamide gel electrophoresis or capillary electrophoresis similar to a polymerase extension product which is about 90 bases long.

10. A method for determining the sequence of a DNA template which comprises
 (a) preparing a sequencing reaction mixture comprising
  (i) the DNA template;
  (ii) a primer which is a complementary to a 3' region of the DNA template;
  (iii) unlabeled deoxyribonucleoside triphosphates;
  (iv) at least one dideoxyribonucleoside triphosphate;
  (v) a DNA polymerase;
  (vi) a substance labeled with a fluorescent dye, wherein the substance is a deoxyribonucleoside triphosphate, the primer, or the at least one dideoxyribonucleoside triphosphate; and
  (vii) an aqueous buffer
 (b) treating the sequencing reaction mixture under conditions and for a time sufficient to synthesize a series of polymerase extension products of different lengths, wherein each of the polymerase extension products comprises a sequence of nucleotides complementary to at least part of the DNA template and wherein at least one of the nucleotides in each extension product comprises the fluorescent dye;

le;.5q(c) mixing the polymerase extension products with a denaturing solution comprising formamide, wherein the denaturing solution further comprises at least one compound that reduces degradation of the nucleotide comprising the fluorescent dye, wherein the at least one compound is not alkaline ethylenediaminetetraacetic acid (EDTA); and (d) analyzing the denatured polymerase extension products to determine the sequence of nucleotides in the DNA template.

11. The method of claim 10, wherein the at least one compound in the denaturing solution is selected from the group consisting of a base, a buffer, and a reducing agent.

12. The method of claim 11, wherein the at least one compound of step (c) is dithiothreitol (DTT).

13. The method of claim 12, wherein the denaturing solution further comprises $NaHCO_3$.

14. The method of claim 11, wherein the fluorescent dye is a fluorescent energy transfer dye.

15. The method of claim 14, wherein the fluorescent energy transfer dye is 5CFB-dR110-2.

16. The method of claim 15, wherein the conditions of step (b) are conducive for cycle amplification of the polymerase extension products.

17. The method of claim 16, wherein the labeled nucleotide is a dideoxyribonucleotide.

18. The method of claim 17, wherein the labeled dideoxyribonucleotide is ddG-EO-5CFB-dR110-2.

19. The method of claim 3, wherein the DTT is added at 5 mM and the $NaHCO_3$ is added at 0.3 mM.

20. The method of claim 4, wherein the DTT is added at 5 mM and the $NaHCO_3$ is added at 0.3 mM.

21. The method of claim 12, wherein the DTT is present at 5 mM and the $NaHCO_3$ is present at 0.3 mM.

* * * * *

UNITED STATES PATENT AND TRADEMARK OFFICE
CERTIFICATE OF CORRECTION

PATENT NO. : 6,232,076 B1  Page 1 of 1
DATED : May 15, 2001
INVENTOR(S) : Vincent P. Schulz It is certified that error appears in the above-identified patent and that said Letters Patent is hereby corrected as shown below:

<u>Column 19,</u>
Line 49, replace "a" with -- than --; and

<u>Colum 21,</u>
Line 1, delete "le;5q".

Signed and Sealed this

Thirteenth Day of November, 2001

Attest:

*Nicholas P. Godici*

NICHOLAS P. GODICI
*Attesting Officer*  *Acting Director of the United States Patent and Trademark Office*

SEQUENCE LISTING

<160> NUMBER OF SEQ ID NOS: 2

<210> SEQ ID NO 1
<211> LENGTH: 660
<212> TYPE: DNA
<213> ORGANISM: M13 Virus

<400> SEQUENCE: 1

| | | | | | | |
|---|---|---|---|---|---|---|
| cgacggccag | tgccaagctt | gcatgcctgc | aggtcgactc | tagaggatcc | ccgggtaccg | 60 |
| agctcgaatt | cgtaatcatg | gtcatagctg | tttcctgtgt | gaaattgtta | tccgctcaca | 120 |
| attccacaca | acatacgagc | cggaagcata | aagtgtaaag | cctggggtgc | ctaatgagtg | 180 |
| agctaactca | cattaattgc | gttgcgctca | ctgcccgctt | tccagtcggg | aaacctgtcg | 240 |
| tgccagctgc | attaatgaat | cggccaacgc | gcggggagag | gcggtttgcg | tattgggcgc | 300 |
| cagggtggtt | tttcttttca | ccagcgagac | gggcaacagc | tgattgccct | tcaccgcctg | 360 |
| gccctgagag | agttgcagca | agcggtccac | gctggtttgc | cccagcaggc | gaaaatcctg | 420 |
| tttgatggtg | gttccgaaat | cggcaaaatc | ccttataaat | caaaagaata | gcccgagata | 480 |
| gggttgagtg | ttgttccagt | ttggaacaag | agtccactat | taaagaacgt | ggactccaac | 540 |
| gtcaaagggc | gaaaaaccgt | ctatcagggc | gatggcccac | tacgtgaacc | atcacccaaa | 600 |
| tcaagttttt | tggggtcgag | gtgccgtaaa | gcactaaatc | ggaaccctaa | agggagcccc | 660 |

<210> SEQ ID NO 2
<211> LENGTH: 18
<212> TYPE: DNA
<213> ORGANISM: M13 Virus

<400> SEQUENCE: 2

| | |
|---|---|
| tgtaaaacga cggccagt | 18 |